(12) United States Patent
Sham et al.

(10) Patent No.: US 10,835,183 B2
(45) Date of Patent: Nov. 17, 2020

(54) APPARATUS AND METHOD FOR INTRAVASCULAR MEASUREMENTS

(71) Applicant: Zurich Medical Corporation, St. Paul, MN (US)

(72) Inventors: Kin-Joe Sham, Blaine, MN (US); James V. Donadio, III, Victoria, MN (US); Charles C. H. Chan, Minneapolis, MN (US)

(73) Assignee: ZURICH MEDICAL CORPORATION, St. Paul, MN (US)

( * ) Notice: Subject to any disclaimer, the term of this patent is extended or adjusted under 35 U.S.C. 154(b) by 562 days.

(21) Appl. No.: 14/747,692

(22) Filed: Jun. 23, 2015

(65) Prior Publication Data

US 2015/0289815 A1    Oct. 15, 2015

Related U.S. Application Data

(63) Continuation-in-part of application No. 14/321,776, filed on Jul. 1, 2014.

(Continued)

(51) Int. Cl.
*A61B 5/00* (2006.01)
*A61M 25/09* (2006.01)
(Continued)

(52) U.S. Cl.
CPC ........ *A61B 5/6851* (2013.01); *A61B 5/02007* (2013.01); *A61B 5/0215* (2013.01);
(Continued)

(58) Field of Classification Search
CPC . A61B 5/6851; A61B 5/0215; A61B 5/02007; A61B 5/742; A61B 2560/04;
(Continued)

(56) References Cited

U.S. PATENT DOCUMENTS

| 4,691,709 A | 9/1987 | Cohen |
| 4,777,951 A | 10/1988 | Cribier et al. |

(Continued)

FOREIGN PATENT DOCUMENTS

| EP | 3879615 A1 | 11/1998 |
| EP | 1125548 A1 | 8/2001 |

(Continued)

OTHER PUBLICATIONS

US 8,180,431 B2, 05/2012, Altmann et al. (withdrawn)
(Continued)

*Primary Examiner* — Jacqueline Cheng
*Assistant Examiner* — Tho Q Tran
(74) *Attorney, Agent, or Firm* — Carter, DeLuca & Farrell LLP

(57) ABSTRACT

Intravascular diagnosis apparatus and methods are disclosed. In one aspect of the disclosed technology, a monitoring guidewire includes a core wire having or made of one or more of MP35N, L605, Elgiloy, and an alloy of nickel, cobalt, molybdenum and chromium, a sensor disposed in a distal region of the core wire, and a housing substantially coextensive with the core wire and surrounding the core wire, the housing being more flexible than the core wire for at least the distal portion of the housing.

8 Claims, 14 Drawing Sheets

Related U.S. Application Data

(60) Provisional application No. 61/841,517, filed on Jul. 1, 2013, provisional application No. 61/985,858, filed on Apr. 29, 2014.

(51) Int. Cl.
    *A61B 5/0215*     (2006.01)
    *A61B 5/02*     (2006.01)

(52) U.S. Cl.
    CPC ............ *A61B 5/742* (2013.01); *A61M 25/09* (2013.01); *A61B 2560/0204* (2013.01); *A61B 2560/04* (2013.01); *A61M 2025/09091* (2013.01); *A61M 2025/09108* (2013.01)

(58) Field of Classification Search
    CPC .......... A61B 2560/0204; A61M 25/09; A61M 25/09091; A61M 2025/09108
    See application file for complete search history.

(56) References Cited

U.S. PATENT DOCUMENTS

| | | |
|---|---|---|
| 4,867,173 A | 9/1989 | Leoni |
| 4,884,579 A | 12/1989 | Engelson |
| 4,901,731 A | 2/1990 | Millar |
| 4,928,693 A | 5/1990 | Goodin et al. |
| 4,936,310 A | 6/1990 | Engstrom et al. |
| 4,941,473 A | 7/1990 | Tenerz et al. |
| 4,953,553 A | 9/1990 | Tremulis |
| 5,040,543 A | 8/1991 | Badera et al. |
| 5,063,935 A | 11/1991 | Gambale |
| 5,065,769 A | 11/1991 | de Toledo |
| 5,113,868 A | 5/1992 | Wise et al. |
| 5,163,445 A | 11/1992 | Christian et al. |
| 5,178,153 A | 1/1993 | Einzig |
| 5,226,421 A | 7/1993 | Frisbie et al. |
| 5,226,423 A | 7/1993 | Tenerz et al. |
| 5,308,324 A | 5/1994 | Hammerslag et al. |
| 5,313,957 A | 5/1994 | Little |
| 5,358,409 A | 10/1994 | Obara |
| 5,412,994 A | 5/1995 | Cook et al. |
| 5,413,508 A | 5/1995 | Obara |
| 5,441,055 A * | 8/1995 | Ales ................. A61M 25/0905 600/434 |
| 5,450,853 A * | 9/1995 | Hastings .............. A61B 5/0215 600/488 |
| 5,509,411 A | 4/1996 | Littmann et al. |
| 5,517,989 A | 5/1996 | Frisbie et al. |
| 5,549,109 A | 8/1996 | Samson et al. |
| 5,668,320 A | 9/1997 | Cowan |
| RE35,648 E | 11/1997 | Tenerz et al. |
| 5,685,322 A | 11/1997 | Sung et al. |
| 5,690,120 A | 11/1997 | Jacobsen et al. |
| 5,699,796 A | 12/1997 | Littmann et al. |
| 5,715,827 A | 2/1998 | Corl et al. |
| 5,797,856 A | 8/1998 | Frisbie et al. |
| 5,807,265 A | 9/1998 | Itoigawa et al. |
| 5,873,835 A | 2/1999 | Hastings et al. |
| 5,916,177 A | 6/1999 | Schwager |
| 5,938,624 A | 8/1999 | Akerfeldt et al. |
| 6,004,279 A | 12/1999 | Crowley et al. |
| 6,017,319 A | 1/2000 | Jacobsen et al. |
| 6,089,103 A | 7/2000 | Smith |
| 6,106,476 A | 8/2000 | Carl et al. |
| 6,112,598 A | 9/2000 | Tenerz et al. |
| 6,142,958 A | 11/2000 | Hammarstrom et al. |
| 6,162,182 A | 12/2000 | Cole |
| 6,167,763 B1 | 1/2001 | Tenerz et al. |
| 6,183,424 B1 | 2/2001 | Schwager |
| 6,193,669 B1 | 2/2001 | Degany et al. |
| 6,196,980 B1 | 3/2001 | Akerfeldt et al. |
| 6,210,339 B1 | 4/2001 | Kiepen et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,336,906 B1 | 1/2002 | Hammarstroem et al. |
| 6,343,514 B1 | 2/2002 | Smith |
| 6,379,308 B1 | 4/2002 | Brockway et al. |
| 6,409,677 B1 | 6/2002 | Tulkki |
| 6,428,336 B1 | 8/2002 | Akerfeldt |
| 6,440,088 B1 | 8/2002 | Jacobsen et al. |
| 6,461,301 B2 | 10/2002 | Smith |
| 6,471,656 B1 | 10/2002 | Shalman et al. |
| 6,565,514 B2 | 5/2003 | Svanerudh et al. |
| 6,579,246 B2 | 6/2003 | Jacobsen et al. |
| 6,615,067 B2 | 9/2003 | Hoek et al. |
| 6,615,667 B2 | 9/2003 | Smith |
| 6,672,172 B2 | 1/2004 | Tulkki et al. |
| 6,767,327 B1 | 7/2004 | Carl et al. |
| 6,779,257 B2 | 8/2004 | Kiepen et al. |
| 6,908,442 B2 | 6/2005 | von Malmborg et al. |
| 6,926,674 B2 | 8/2005 | Tenerz et al. |
| 6,976,965 B2 | 12/2005 | Corl et al. |
| 7,017,420 B2 | 3/2006 | Kalvesten et al. |
| 7,018,346 B2 | 3/2006 | Griffin et al. |
| 7,097,620 B2 | 8/2006 | Corl et al. |
| 7,134,994 B2 | 11/2006 | Alpert et al. |
| 7,263,894 B2 | 9/2007 | Tenerz |
| RE39,863 E | 10/2007 | Smith |
| 7,326,204 B2 | 2/2008 | Paul et al. |
| 7,450,989 B2 | 11/2008 | Svanerudh |
| RE40,608 E | 12/2008 | Glover et al. |
| 7,628,763 B2 | 12/2009 | Noriega et al. |
| 7,676,910 B2 | 3/2010 | Kiepen et al. |
| 7,706,891 B2 | 4/2010 | Hastings et al. |
| 7,711,413 B2 | 5/2010 | Feldman et al. |
| 7,774,051 B2 | 8/2010 | Voth |
| 7,775,992 B2 | 8/2010 | von Malmborg et al. |
| 7,857,810 B2 | 12/2010 | Wang et al. |
| 7,878,984 B2 | 2/2011 | Jacobsen et al. |
| 7,914,466 B2 | 3/2011 | Davis et al. |
| 7,931,603 B2 | 4/2011 | Von Malmborg et al. |
| 7,967,761 B2 | 6/2011 | Smith |
| 7,967,762 B2 | 6/2011 | Corl et al. |
| 7,988,633 B2 | 8/2011 | Hossack et al. |
| 7,988,639 B2 | 8/2011 | Starks |
| 7,998,089 B2 | 8/2011 | Smith |
| 8,012,145 B2 | 9/2011 | Cawley |
| 8,043,312 B2 | 10/2011 | Noriega et al. |
| 8,052,683 B2 | 11/2011 | Podmore et al. |
| 8,075,490 B2 | 12/2011 | Lofgren et al. |
| 8,105,246 B2 | 1/2012 | Voeller et al. |
| 8,162,856 B2 | 4/2012 | Williams et al. |
| 8,162,934 B2 | 4/2012 | Potter |
| 8,174,395 B2 | 5/2012 | Samuelsson et al. |
| 8,182,466 B2 | 5/2012 | Stehr et al. |
| 8,216,151 B2 | 7/2012 | Smith |
| 8,229,545 B2 | 7/2012 | Afonso |
| 8,231,537 B2 | 7/2012 | Ahmed et al. |
| 8,277,386 B2 | 10/2012 | Ahmed et al. |
| 8,317,715 B2 | 11/2012 | Belleville et al. |
| 8,340,766 B2 | 12/2012 | Ryu et al. |
| 8,343,076 B2 | 1/2013 | Sela et al. |
| 8,376,991 B2 | 2/2013 | Kauphusman et al. |
| 8,382,689 B2 | 2/2013 | Sliwa et al. |
| 8,391,956 B2 | 3/2013 | Zellers et al. |
| 8,403,868 B2 | 3/2013 | Von Malmborg et al. |
| 8,414,568 B2 | 4/2013 | Harlan |
| 8,419,647 B2 | 4/2013 | Corl et al. |
| 8,437,832 B2 | 5/2013 | Govari et al. |
| 8,468,919 B2 | 6/2013 | Christian et al. |
| 8,480,636 B2 | 7/2013 | Khieu et al. |
| 8,485,985 B2 | 7/2013 | Manstrom et al. |
| 8,551,020 B2 | 10/2013 | Chen et al. |
| 8,551,021 B2 | 10/2013 | Voeller et al. |
| 8,556,914 B2 | 10/2013 | Vrba |
| 8,641,633 B2 | 2/2014 | Smith |
| 8,657,789 B2 | 2/2014 | Guo et al. |
| 8,684,962 B2 | 4/2014 | Kirschenman et al. |
| 8,684,999 B2 | 4/2014 | Tegg et al. |
| 8,696,584 B2 | 4/2014 | Kassab |
| 8,702,613 B2 | 4/2014 | Kassab |
| 8,734,440 B2 | 5/2014 | Wu |

(56) References Cited

U.S. PATENT DOCUMENTS

| | | | |
|---|---|---|---|
| 8,734,699 B2 | 5/2014 | Heideman et al. | |
| 8,755,860 B2 | 6/2014 | Paul et al. | |
| 8,758,333 B2 | 6/2014 | Harlan | |
| 8,764,683 B2 | 7/2014 | Meller et al. | |
| 8,777,929 B2 | 7/2014 | Schneider et al. | |
| 8,795,254 B2 | 8/2014 | Layman et al. | |
| 8,818,485 B2 | 8/2014 | Govari et al. | |
| 8,858,591 B2 | 10/2014 | Preinitz et al. | |
| 8,915,865 B2 | 12/2014 | Jacobsen et al. | |
| 8,936,559 B2 | 1/2015 | Strommer et al. | |
| 8,979,837 B2 | 3/2015 | de la Rama et al. | |
| 8,989,849 B2 | 3/2015 | Milner et al. | |
| 8,998,826 B2 | 4/2015 | Hauck et al. | |
| 9,301,810 B2 | 4/2016 | Amiri et al. | |
| 9,326,756 B2 | 5/2016 | Stangenes et al. | |
| 2001/0009980 A1* | 7/2001 | Richardson | A61M 25/09 600/585 |
| 2002/0013540 A1* | 1/2002 | Jacobsen | A61M 25/09 600/585 |
| 2002/0072880 A1 | 6/2002 | Svanerudh et al. | |
| 2003/0023190 A1 | 1/2003 | Cox | |
| 2003/0032886 A1 | 2/2003 | Dgany et al. | |
| 2003/0069522 A1 | 4/2003 | Jacobsen et al. | |
| 2004/0167436 A1* | 8/2004 | Reynolds | A61M 25/09 600/585 |
| 2004/0225232 A1* | 11/2004 | Malmborg | A61B 5/0215 600/585 |
| 2005/0020974 A1 | 1/2005 | Noriega | |
| 2005/0085847 A1* | 4/2005 | Galdonik | A61F 2/01 606/200 |
| 2005/0096566 A1 | 5/2005 | Arnott | |
| 2006/0052700 A1 | 3/2006 | Svanerudh | |
| 2006/0074442 A1* | 4/2006 | Noriega | A61B 17/32002 606/159 |
| 2006/0135864 A1 | 6/2006 | Westerlund et al. | |
| 2007/0010762 A1* | 1/2007 | Ressemann | A61M 25/09 600/585 |
| 2007/0078352 A1 | 4/2007 | Pijls | |
| 2007/0185485 A1 | 8/2007 | Hauck et al. | |
| 2007/0255144 A1 | 11/2007 | Tulkki et al. | |
| 2007/0255145 A1* | 11/2007 | Smith | A61B 5/0215 600/485 |
| 2007/0270741 A1 | 11/2007 | Hassett et al. | |
| 2007/0299403 A1 | 12/2007 | Crowe et al. | |
| 2007/0299424 A1 | 12/2007 | Cumming et al. | |
| 2007/0299436 A1 | 12/2007 | Podmore et al. | |
| 2007/0299438 A1 | 12/2007 | Holzbaur et al. | |
| 2008/0091193 A1 | 4/2008 | Kauphusman et al. | |
| 2008/0140101 A1 | 6/2008 | Carley et al. | |
| 2008/0200773 A1 | 8/2008 | Pop | |
| 2008/0221438 A1 | 9/2008 | Chen et al. | |
| 2008/0221601 A1 | 9/2008 | Huynh et al. | |
| 2008/0262474 A1 | 10/2008 | Northrop | |
| 2009/0036832 A1 | 2/2009 | Skujins et al. | |
| 2009/0171345 A1 | 7/2009 | Miller et al. | |
| 2009/0177119 A1 | 7/2009 | Heidner et al. | |
| 2010/0125197 A1 | 5/2010 | Fishel | |
| 2010/0137736 A1 | 6/2010 | Addington et al. | |
| 2010/0228112 A1 | 9/2010 | Von Malmborg | |
| 2010/0234698 A1 | 9/2010 | Manstrom et al. | |
| 2010/0268038 A1 | 10/2010 | Smith | |
| 2010/0305458 A1 | 12/2010 | Pfeiffer et al. | |
| 2010/0318000 A1 | 12/2010 | Von Malmborg et al. | |
| 2011/0004198 A1 | 1/2011 | Hoch | |
| 2011/0009694 A1 | 1/2011 | Schultz et al. | |
| 2011/0054487 A1 | 3/2011 | Farnan | |
| 2011/0152721 A1 | 6/2011 | Sela et al. | |
| 2011/0160680 A1 | 6/2011 | Cage et al. | |
| 2011/0160832 A1 | 6/2011 | Cohen | |
| 2011/0245693 A1* | 10/2011 | Hastings | A61B 5/0215 600/486 |
| 2012/0172731 A1 | 7/2012 | Smith | |
| 2012/0278008 A1 | 11/2012 | Davies et al. | |
| 2012/0289808 A1 | 11/2012 | Hubinette | |
| 2013/0046190 A1 | 2/2013 | Davies | |
| 2013/0046202 A1 | 2/2013 | Tsunezumi et al. | |
| 2013/0102927 A1 | 4/2013 | Hilmersson | |
| 2013/0116579 A1 | 5/2013 | Svanerudh | |
| 2013/0131523 A1 | 5/2013 | Suchecki et al. | |
| 2013/0131663 A1 | 5/2013 | Govari et al. | |
| 2013/0172782 A1 | 7/2013 | Hilmersson | |
| 2013/0190633 A1 | 7/2013 | Dorando et al. | |
| 2013/0218032 A1 | 8/2013 | Belleville | |
| 2013/0237864 A1* | 9/2013 | Mazar | A61B 5/0215 600/488 |
| 2013/0274618 A1 | 10/2013 | Hou et al. | |
| 2013/0296692 A1* | 11/2013 | Vanney | A61M 25/09 600/424 |
| 2013/0296718 A1* | 11/2013 | Ranganathan | A61B 5/02 600/481 |
| 2013/0296722 A1 | 11/2013 | Warnking et al. | |
| 2013/0317372 A1 | 11/2013 | Eberle et al. | |
| 2013/0324842 A1 | 12/2013 | Mittal et al. | |
| 2013/0338538 A1 | 12/2013 | Park et al. | |
| 2014/0005558 A1 | 1/2014 | Gregorich | |
| 2014/0039325 A1 | 2/2014 | Belleville | |
| 2014/0058275 A1 | 2/2014 | Gregorich et al. | |
| 2014/0058715 A1 | 2/2014 | Sharma et al. | |
| 2014/0066790 A1 | 3/2014 | Burkett et al. | |
| 2014/0066791 A1 | 3/2014 | Burkett | |
| 2014/0081244 A1 | 3/2014 | Voeller et al. | |
| 2014/0107624 A1 | 4/2014 | Belleville | |
| 2014/0180028 A1 | 6/2014 | Burkett | |
| 2014/0187979 A1 | 7/2014 | Burkett | |
| 2014/0187983 A1 | 7/2014 | Anderson | |
| 2014/0276109 A1 | 9/2014 | Gregorich | |
| 2014/0276117 A1 | 9/2014 | Burkett | |
| 2014/0276223 A1 | 9/2014 | Gustafsson | |
| 2014/0276226 A1 | 9/2014 | Meller et al. | |
| 2014/0336620 A1 | 11/2014 | Layman et al. | |
| 2015/0005648 A1 | 1/2015 | Sham et al. | |
| 2015/0032027 A1 | 1/2015 | Lupton | |
| 2015/0148693 A1 | 5/2015 | Burkett | |
| 2016/0303354 A1 | 10/2016 | Burkett | |

FOREIGN PATENT DOCUMENTS

| | | |
|---|---|---|
| EP | 1310215 A1 | 5/2003 |
| EP | 0877574 B1 | 10/2003 |
| EP | 0973438 B1 | 11/2003 |
| EP | 1433429 A2 | 6/2004 |
| EP | 1076511 B1 | 8/2004 |
| EP | 1125548 B1 | 4/2005 |
| EP | 0968547 B1 | 8/2005 |
| EP | 1012912 B1 | 12/2005 |
| EP | 0907335 B1 | 9/2006 |
| EP | 1837638 A1 | 9/2007 |
| EP | 1849409 A1 | 10/2007 |
| EP | 1055392 B1 | 3/2008 |
| EP | 1922988 A1 | 5/2008 |
| EP | 2042091 A1 | 4/2009 |
| EP | 1608418 B1 | 7/2009 |
| SE | 523337 C2 | 4/2004 |
| WO | 2001021057 A2 | 3/2001 |
| WO | 2003022122 A2 | 3/2003 |
| WO | 2009020836 A1 | 2/2009 |
| WO | 2011110817 A2 | 9/2011 |
| WO | 2012000798 A1 | 1/2012 |
| WO | 2012041905 A1 | 4/2012 |
| WO | 2012061935 A1 | 5/2012 |
| WO | 2012091783 A1 | 7/2012 |
| WO | 2012173697 A1 | 12/2012 |
| WO | 2013028737 A1 | 2/2013 |
| WO | 2013092969 A2 | 6/2013 |
| WO | 2013164682 A1 | 11/2013 |
| WO | 2013169451 A1 | 11/2013 |
| WO | 2014005095 A1 | 1/2014 |
| WO | 2014025255 A1 | 2/2014 |
| WO | 2014043704 A1 | 3/2014 |
| WO | 2014105578 A1 | 7/2014 |

(56) References Cited

FOREIGN PATENT DOCUMENTS

| | | |
|---|---|---|
| WO | 2014140883 A1 | 9/2014 |
| WO | 2014149688 A1 | 9/2014 |

OTHER PUBLICATIONS

Partial European Search Report issued in corresponding application No. 14820180 dated Jan. 10, 2017.
Notification of Transmittal of the International Search Report and the Written Opinion of the International Searching Authority, or the Declaration issued in corresponding application No. PCT/US2016/037389 dated Sep. 27, 2016.
B. Nudell, et al., "Fame II Good for FFR and PCI", Credit Suisse Securities Research & Analytics, Americas/United States, Equity Research, Medical Supplies & Devices, Aug. 28, 2012, pp. 1-9.
M. Weinstein, et al. "Cardiovascular Devices, Fame II: The Drumbeat of Data Supporting Broader FFR Use Continues", J.P. Morgan North America Equity Research, Aug. 28, 2012 pp. 1-6.
"PressureWire(TM) Certus(TM) with Agile Tip", St. Jude Medical, 2012, pp. 1-2.
S. Sen, et al., "Development and Validation of a New Adenosine-Independent Index of Stenosis Severity From Coronary Wave-Intensity Analysis", Journal of the American College of Cardiology, vol. 59, No. 15, Apr. 10, 2012, pp. 1392-1402.
R. Petraco et al., "Classification performance of instantaneous wave-free ratio (iFR) and fractional flow reserve in a clinical population of intermediate coronary stenoses: results of the ADVISE registry", EuroIntervention 2013; 9: 91-101.
De Bruyne et al, "Fractional Flow Reserve-Guided PCI versus Medical Therapy in Stable Coronary Disease", The New England Journal of Medicine, vol. 367, No. 11, Sep. 13, 2012, pp. 991-1001.
"St. Jude Medical executive: FAMI II trial's FFR products showing 'significant growth'", http://medcitynews.com/2012/01/fame-ii-trials-ffr-products-showing-significant-growth-st- . . . Jan. 19, 2012.
P. Tonino et al., "Fractional Flow Reserve versus Angiography for Guiding Percutaneous Coronary Intervention", The New England Journal of Medicine, vol. 360, No. 3, Jan. 15, 2009, pp. 213-224.
R. Petraco et al., "Hybrid iFR-FFR decision-making strategy: implications for enhancing universal adoption of physiology-guided coronary revascularisation", EuroIntervention 2013; 8:1157-1165.
Written Opinion of the International Searching Authority issued in corresponding application No. PCT/US14/45171dated Jan. 21, 2015.
PCT International Search Report issued in corresponding application No. PCT/US2014/045171 dated Jan. 21, 2015.
Volcano Announces Preliminary Results from the ADVISE II Study and Inclusion in the SYNTAX2 Trial During Hot Line Late Breaking Clinical Trial Sessions at EuroPCR 2013, PR Newswire—Thursday, May 23, 2013 (<http://m.yahoo.com/w/legobpengine/finance/news/volcano-announces-preliminary-results-advise-083000929.html?.intl=us&lang=en-us>).
Instructions for use PrimeWire Presige(R) Plus, Pressure Guide Wire, Models: 9185/9185J-9300/9300J English, Volcano, Aug. 2012.
"Importance of FFR in Treatment of Coronary Artery Disease Confirmed by New PCI Guidelines", St. Jude Medical News Release, Dec. 16, 2009, pp. 1-3.
Instructions for Use for PressureWire(TM) Aeris (TM) Wireless FFR Measurement System, St. Jude Medical, Nov. 18, 2010. pp. 1-17.
Instructions for Use for PressureWire(TM) Receiver, St. Jude Medical, Oct. 18, 2010, pp. 1-15.
Quantien(TM) Integrated FFR Platform, St. Jude Medical, Jul. 10, 2013 (http://professional.sjm.com/products/vas/intravascular-diagnostics-imaging/ffr/quantien).
Quantien(TM) Integrated FFR Platform, Dicom Conformance Statement Model Quantien—Cardiology, Revision A, St. Jude Medical, 2012, pp. 1-29.
C. Berry et al., "VERIFY (VERification of Instantaneous Wave-Free Ratio and Fractional Flow Reserve for the Assessment of Coronary Artery Stenosis Severity in Every Practice)", Journal of the American College of Cardiology, vol. 16, No. 13, 2013, pp. 1421-1427.
"Advise Study Results Demonstrate the Instant Wave-Free Ratio (TM), a Vasodilate Free Measure of Stenosis Severity, is Comparable to FFR", Volcano Corporation and Imperial College London Support Study Presented During Late Breaking Clinical Trial Session at TCT Nov. 14, 2011.
Instructions for Use for "Combowire(R) Pressure/Flow Guide Wire REF 9500 Series", Volcano Corporation, Revision Date: Feb. 2012, pp. 1-4.
Instructions for Use for "FloWire(R) Doppler Guide Wire REF 1400 Series—FloWire", Volcano Corporation, Revision Date Feb. 2012.
Instructions for use for "PrimeWire PRESTIGE(R) Pressue Guide Wire", Models: 818518185J-8300/8300J, Volcano Corporation, Revision Date Nov. 2012.
Instructions for use for "PrimeWire Prestige(R) Plus Pressure Guide Wire", Models: 9185/9185J-9300/9300J, Volcano Corporation, Revision Date Aug. 2012.
Instructions for use for "Veratta(R) Pressue Guide Wire", Models: 10185/10185J—10300/10300J, Volcano Corporation, Revision Date Jan. 2014.
InvestorPlace, "Volcano, St. Jude: 2 hearts beat as one. The Companies dominate a potential $2 billion test market." Jan. 14, 2013 (http://money.msn.com/top-stocks/post.aspx?post=3bb89ca7-9959-4173-910e-eee3fc37a742).
J. Brosky, "Drug-free lesion assessment rivals fractional flow reserve", Medical Device Daily, EuroPCR May 29, 2013 http://www.medicaldevicedaily.com/servlet/com.accumedia.web.Dispatcher?next=bioWorl . . . ).
Volcano Corporation S5/S5i (Chinese), www.dragonmedical.com, retrieved from internet Dec. 22, 2013.
"Wi-Box(TM) Cath Lab Installation and FAQ Dec. 2011", St. Jude Medical, 2011.
"FFR and PressureWire(TM) Certus", St. Jude Medical, p. 1-34, retrieved from internet Feb. 9, 2014.
"SJM PressureWire Certus IFU (2)", St. Jude Medical, pp. 4-13, www.sjm.com, retrieved from internet Jun. 29, 2013.
"SJM RadiAnalyzer IFU", 20645 IFU RANXpress ENG R03 2010-12.indd, St. Jude Medical, pp. 3-48; 2010.
"PressureWire(TM) Agile Tip Technology", St. Jude Medical, p. 1-15; 2012.
Supplementary European Search Report issued by the European Patent Office dated Jan. 2, 2019 in corresponding European Patent Application No. 16815059.7.
Non-Final Office Action dated Sep. 19, 2018 in U.S. Appl. No. 14/930,168 (10 pages).
Final Office Action dated Jun. 28, 2019 in U.S. Appl. No. 14/930,168 (11 pages).
Examination Report issued by the Australian Patent Office dated Mar. 19, 2020 in corresponding Australian Patent Application No. 2016282495.

* cited by examiner

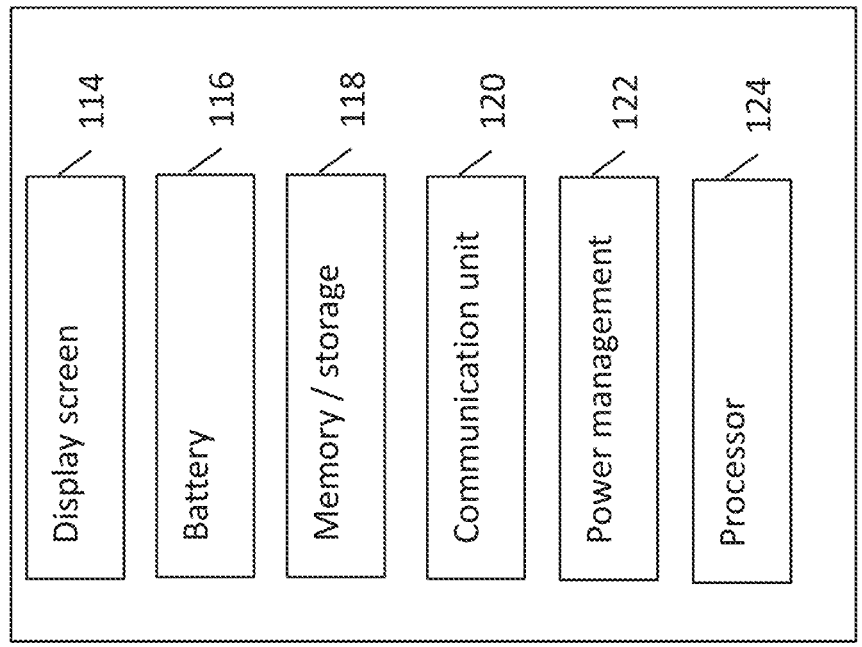
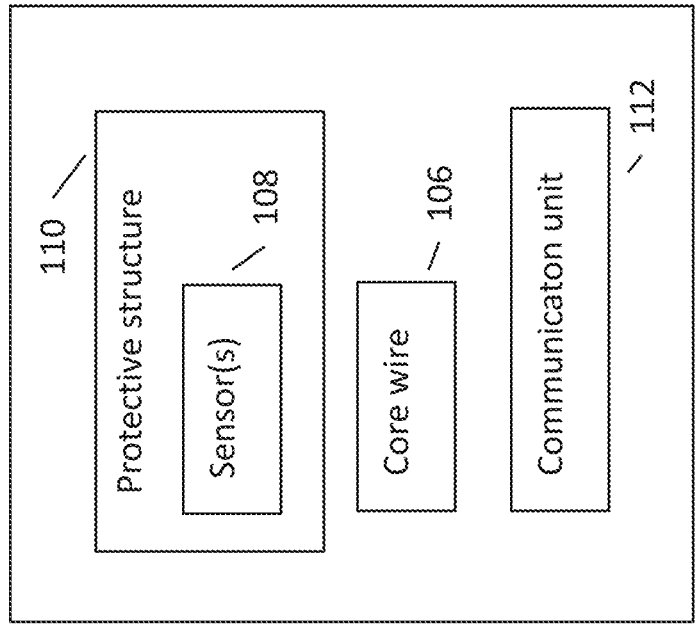
FIG. 1

APPARATUS AND METHOD FOR INTRAVASCULAR MEASUREMENTS

CROSS-REFERENCE TO RELATED APPLICATIONS

This application is a continuation-in-part of U.S. patent application Ser. No. 14/321,776, filed Jul. 1, 2014, which claims priority to U.S. Provisional Application No. 61/985,858, filed Apr. 29, 2014, and to U.S. Provisional Application No. 61/841,517, filed Jul. 1, 2013. The entire contents of each and every priority application are hereby incorporated by reference herein.

FIELD OF THE INVENTION

The disclosed technology relates to intravascular diagnosis. More particularly, the disclosed technology relates to diagnosing the severity of stenosis in the vasculature of a patient.

BACKGROUND

Reduced blood flow due to atherosclerotic occlusion of vessels is a major cause of vascular diseases. Pressure measurements in arterial vessels and particularly in coronary arteries prior to treatment have been used for lesion characterization and treatment selection. More specifically, pressure gradient across a lesion has been clinically used as an indicator for lesion severity. Measurements made during and after treatment allow one to assess therapy efficacy. Existing equipment for monitoring intravascular measurements have multiple, separate parts and bulky monitors. There is, accordingly, continuing interest in improved monitoring equipment.

SUMMARY

The disclosed technology relates to diagnosing the severity of stenoses in the vasculature of a patient.

In one aspect of the disclosed technology, an apparatus for intravascular diagnosis includes a monitoring guidewire having a core wire and a sensor disposed in a distal region of the core wire, and a portable display unit configured to be disposed after a predetermined number of uses or after a predetermined duration of use. The portable display unit can include a processor and a display screen, where the portable display unit is capable of receiving communication from the monitoring guidewire, is configured to perform computations using the processor based on communications received from the monitoring guidewire, and is configured to display information on the display screen based on the computations.

In one embodiment, the portable display unit includes one or more batteries configured to power the portable display unit. In one embodiment, the one or more batteries can be rechargeable by a power source of the portable display unit and/or a power source external to the portable display unit.

In one embodiment, the portable display unit further includes one or more batteries configured to power the portable display unit for a predetermined duration of use, such that the portable display unit can be configured to be disposed after the one or more batteries are depleted. In one embodiment, the one or more batteries are non-rechargeable. In one embodiment, the portable display unit can be configured to be inoperable after a one uses.

In one aspect of the disclosed technology, the monitoring guidewire can be configured to be disposed after a single use.

In one embodiment, the portable display unit and the monitoring guidewire can communicate wirelessly. In one embodiment, the portable display unit includes a connector configured to establish a communicative connection with the monitoring guidewire. In one embodiment, the connector is configured to establish a mechanical connection with the monitoring guidewire to control the guidewire within a vasculature. In one embodiment, a torquer is configured to engage the monitoring guidewire to control the guidewire within a vasculature.

In one embodiment, the monitoring guidewire includes a housing surrounding the sensor, and the housing can be laser etched to provide flexibility for the housing. In one embodiment, the monitoring guidewire includes a flexible coil surrounding the sensor, with the coil having a relaxed portion over the sensor.

In one aspect of the disclosed technology, the sensor is a pressure sensor and communication from the monitoring guidewire includes measurements from the pressure sensor. The processor of the portable display unit is capable of computing fractional flow reserve based on pressure measurements from only the pressure sensor in the distal region of the core wire.

In one embodiment, the fractional flow reserve is a push-forward fraction flow reserve ("FFR") computed as: $FFR=(P_{sensor}-P_{ra})/(P_{saved}-P_{ra})$, where:

$P_{saved}$ are moving means over time of recorded pressure measurements proximal to a first stenosis, $P_{sensor}$ are moving means over time of real time pressure measurements distal to the first stenosis, and $P_{ra}$ is a constant.

In one embodiment, $P_{saved}$ are moving means over time of recorded pressure measurements proximal to the first stenosis and proximal to a second stenosis. In one embodiment, $P_{sensor}$ are moving means over time of real time pressure measurements distal to the first stenosis and proximal to a second stenosis. In one embodiment, $P_{sensor}$ moving means over time of real time pressure measurements distal to the first stenosis and distal to the second stenosis.

In one embodiment, the fractional flow reserve is a pull-back fraction flow reserve computed as: $FFR=(P_{saved}-)/(P_{sensor}-P_{ra})$, where:

$P_{saved}$ are moving means over time of recorded pressure measurements distal to a first stenosis, $P_{sensor}$ are moving means over time of real time pressure measurements proximal to the first stenosis, and $P_{ra}$ is a constant.

In one embodiment, $P_{sensor}$ are moving means over time of real time pressure measurements proximal to the first stenosis and distal to a second stenosis. In one embodiment, $P_{saved}$ are moving means over time of recorded pressure measurements distal to the first stenosis and distal to a second stenosis. In one embodiment, $P_{sensor}$ are moving means over time of real time pressure measurements proximal to the first stenosis and proximal to the second stenosis.

In one embodiment, the portable display unit displays on the display screen the fractional flow reserve. In one embodiment, the portable display unit displays a graph of the pressure measurements.

In one embodiment, the portable display unit includes a communications port configured to receive communications that include pressure measurements.

In one embodiment, the fractional flow reserve is a pull-back fraction flow reserve computed as: $FFR=(P_{sensor}-P_{ra})/(P_{port}-P_{ra})$, where:

$P_{port}$ are moving means over time of real-time pressure measurements received at the communications port, $P_{sensor}$ are moving means over time of real-time pressure measurements from the pressure sensor disposed in the distal region of the core wire, and $P_{ra}$ is a constant.

In one embodiment, the portable display unit is configured with capability to compute fractional flow reserve in at least two ways: computing fractional flow reserve based on pressure measurements from only the pressure sensor disposed in the distal region of the core wire, and computing fractional flow reserve based on the pressure measurements from the pressure sensor and based on pressure measurements received at a communications port. In one embodiment, the portable display unit can be configured to automatically use one of the at least two ways of computing fractional flow reserve. In one embodiment, the portable display unit can be configured to automatically select one of the ways of computing fractional flow reserve when a condition is present and can be configured to automatically select another of the at least two ways of computing fractional flow reserve when the condition is absent. In one embodiment, the portable display unit can be configured to permit a user to manually select one of the at least two ways of computing fraction flow reserve.

In one aspect of the disclosed technology, an apparatus for intravascular diagnosis includes a monitoring guidewire having a core wire and a sensor disposed in a distal region of the core wire, and a handheld display unit configured to be disposed after a predetermined number of uses or after a predetermined duration of use. The handheld display unit can include a processor and a display screen, where the handheld display unit is capable of receiving communication from the monitoring guidewire, is configured to perform computations using the processor based on communications received from the monitoring guidewire, and is configured to display information on the display screen based on the computations. In one embodiment, the handheld display unit can be equal to or less than 30 cm×30 cm×30 cm in size.

In one aspect of the disclosed technology, an apparatus for intravascular diagnosis includes a monitoring guidewire having a core wire and a sensor disposed in a distal region of the core wire, and a portable display unit capable of receiving communication from the monitoring guidewire. The portable display unit includes a processor and display screen, and is configured to perform computations using the processor based on communications received from the monitoring guidewire and is configured to display information on the display screen based on the computations. The portable display unit has no capability of being turned off after the display screen is turned on, In one aspect of the disclosed technology, a monitoring guidewire includes a core wire having or made of one or more of MP35N, L605, Elgiloy, and an alloy of nickel, cobalt, molybdenum and chromium, a sensor disposed in a distal region of the core wire, and a housing substantially coextensive with the core wire and surrounding the core wire, the housing being more flexible, deflectable or bendable, or less stiff or less rigid, than the core wire for at least the distal portion of the housing.

In one aspect of the disclosed technology, a monitoring guidewire includes a core wire having a first length and including or made of one or more of MP35N, L605, Elgiloy, and an alloy of nickel, cobalt, molybdenum and chromium, a sensor disposed in a distal region of the core wire, and a housing surrounding the core wire and having a second length that is slightly less than the first length.

In one embodiment, the housing is more flexible, deflectable or bendable, or less stiff or less rigid, than the core wire for at most a 40 cm length of the distal portion of the housing. In one embodiment, the housing is more flexible, deflectable or bendable, or less stiff or less rigid, than the core wire for an entire length of the housing.

In one embodiment, the core wire has a diameter of at most 0.007 inches. In one embodiment, the housing includes a hypotube having an outer diameter between 0.013 and 0.014 inches. In one embodiment, the hypotube has an inner diameter less than 0.011 inches.

In one embodiment, the housing further includes an intermediate coil, a protective structure surrounding the sensor, and a distal coil. In one embodiment, the housing further includes a protective structure surrounding the sensor and a distal coil. In one embodiment, the housing further includes a hypotube of approximately 150 cm in length, an intermediate coil, a laser etched hypotube, and a distal coil.

In one embodiment, the core wire and the housing together have a torque response that approximates a torque response of a 0.014 inch workhorse guidewire. In one embodiment, the monitoring guidewire further includes one or more signal wires connected to the sensor and positioned within the housing.

In one aspect of the disclosed technology, a monitoring guidewire includes a core wire, a sensor disposed in a distal region of the core wire, and a hypotube substantially coextensive with the core wire and surrounding the core wire, the hypotube having laser etching along at most 40 cm of the hypotube at a distal portion of the hypotube.

In one aspect of the disclosed technology, a monitoring guidewire includes a core wire having a first length, a sensor disposed in a distal region of the core wire, and a hypotube surrounding the core wire and having a second length that is slightly less than the first length, the hypotube having laser etching along at most a 40 cm length of a distal portion of the hypotube.

In one embodiment, the core wire has a length of approximately 180 cm. In one embodiment, the hypotube has a length of approximately 177 cm. In one embodiment, the hypotube has an outer diameter between 0.013 and 0.014 inches.

In one embodiment, the laser etching is configured to provide the hypotube with a torque response that approximates a torque response of a 0.014 inch workhorse guidewire.

In one aspect of the disclosed technology, a monitoring guidewire includes a hypotube having laser etching along at least a portion of the hypotube and a sensor disposed in a distal region of the hypotube.

In one embodiment, the hypotube has a length of approximately 177 centimeters, wherein the laser etching covers at least a portion of the 177 centimeter length. In one embodiment, the hypotube has an outer diameter of between 0.013 and 0.014 inches.

In one embodiment, the laser etching is configured to provide the hypotube with a torque response that approximates a torque response of a 0.014 inch workhorse guidewire.

In one embodiment, the monitoring guidewire further includes one or more signal wires connected to the sensor and positioned within the hypotube.

These aspects and embodiments of the disclosed technology are exemplary and do not limit the scope of the disclosed technology, which will be apparent from a reading of the following detailed description and the associated drawings.

BRIEF DESCRIPTION OF THE DRAWINGS

FIG. 1 is a block diagram of an exemplary intravascular diagnosis apparatus in accordance with the disclosed technology.

DETAILED DESCRIPTION

Figure 2:
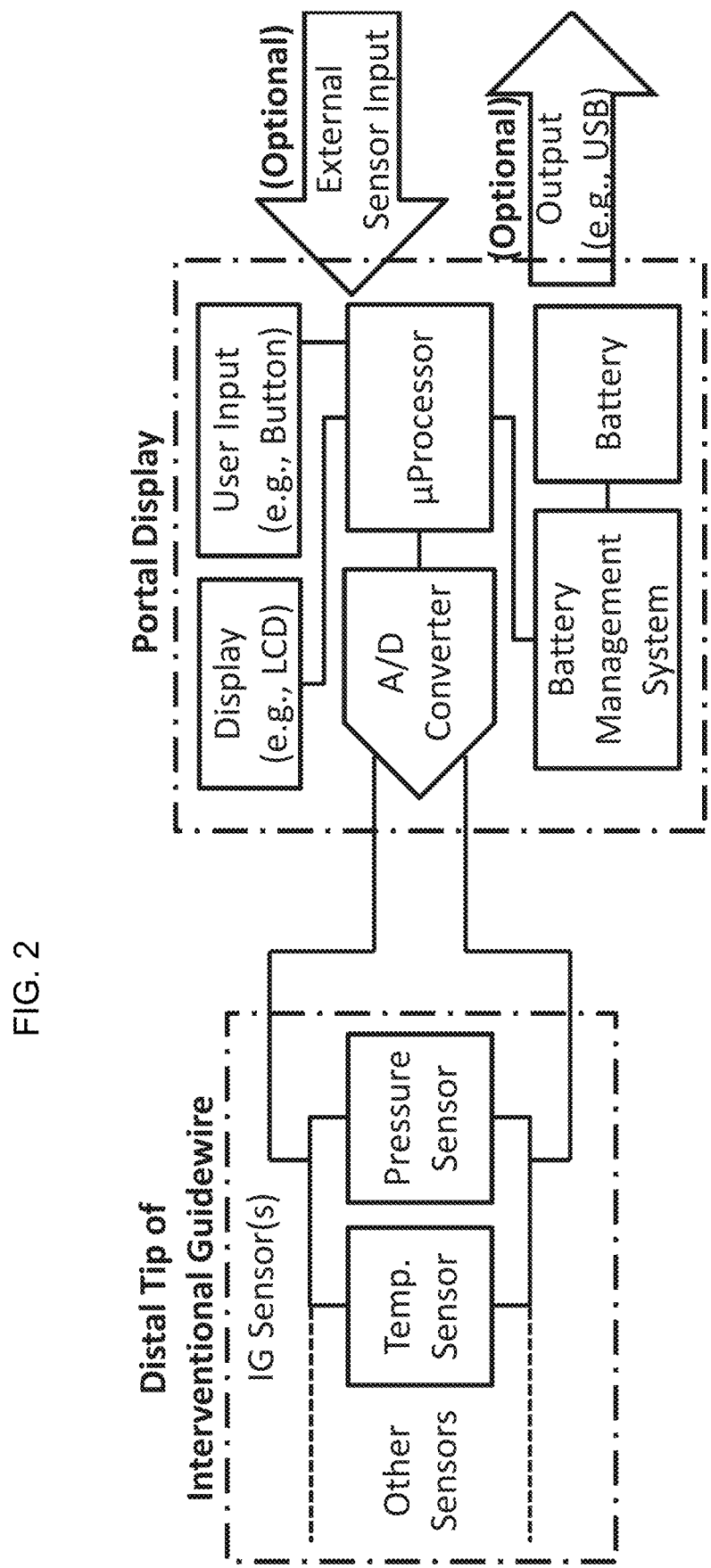
FIG. 2 is a block diagram of an embodiment of the disclosed technology.

The disclosed technology relates to diagnosing the severity of stenosis in the vasculature of a patient. The disclosed technology can be used as an adjunct to conventional angiographic procedures to provide important quantitative measurements of a blood vessel lumen.

Referring now to FIG. 1, there is shown a block diagram of an exemplary intravascular diagnosis apparatus in accordance with the disclosed technology. The illustrated apparatus 100 includes a monitoring guidewire 102 and a portable display unit 104. In one embodiment, the portable display unit 104 can be a handheld display unit, such that any and all aspects and embodiments described herein as being applicable to a portable display unit are also applicable to the disclosed handheld display unit. In one embodiment, the handheld display unit can be equal to or less than 30 cm×30 cm×30 cm in size. In operation, the monitoring guidewire 102 is introduced into the vasculature of a patient with the assistance of conventional interventional equipment known to those skilled in the art, such as catheters. The portable display unit 104 can communicate with the monitoring guidewire 102 and can display information based on the communications received from the monitoring guidewire 102.

The illustrated monitoring guidewire 102 can include several components, including a core wire 106 and one or more sensors 108 disposed in a distal region of the core wire 106. As used herein, the terms "distal" and "proximal" refer to physical directions within a blood vessel lumen. Specifically, in relation to the insertion point of a device into a patient, the term "distal" refers to the direction from the insertion point inwards into a blood vessel, and the term "proximal" refers to the direction from the inside of a blood vessel out towards the insertion point. As used herein, the terms "proximal" and "distal" can also refer to different ends of a device, with "proximal" being the end towards an insertion point into a blood vessel lumen and with "distal" being the end away from the insertion point.

With continuing reference to FIG. 1, the one or more sensors 108 disposed in a distal region of the core wire 106 can include one or more hemodynamic pressure sensors and/or one or more temperature sensors. In one embodiment, the pressure sensor(s) can be a piezo-resistive pressure sensor. As illustrated in FIG. 1, the monitoring guidewire 102 can also include a protective structure 110 surrounding the sensor(s) 108, and can include a communication unit 112. The protective structure 110 of the monitoring guidewire 102 will be described in more detail later herein in connection with FIGS. 5-6.

In one embodiment, the communication unit 112 can employ wireless communication technology such as bluetooth, WiFi (802.11), or any other wireless technology. In one embodiment, the communication unit 112 can be a wireline communication unit that can include one or more wires for communicating electromagnetic signals and/or one or more optical fibers for communicating optical signals. The monitoring guidewire 102 can include other components that are not illustrated, such as a power source, A/D converters, application specific integrated circuits (ASIC), a processor, memory, timing circuitry, and/or other power, analog, or digital circuitry. Such components will be known to those skilled in the art.

Referring now to the illustrated portable display unit 104, the portable display unit 104 can include a display screen 114, one or more batteries 116, memory and/or storage 118, a communication unit 120, power management unit 122, and a processor 124. In one embodiment, the processor 124 can be a general purpose processor or can be an application specific integrated circuit. In one embodiment, the display screen 114 can be a liquid crystal display, an organic light emitting diode display, or another type of display technology. In one embodiment, the memory/storage 118 can include one or more of solid state memory/storage, magnetic disc storage, and/or any other type of memory/storage that will be known to those skilled in the art. In one embodiment, the memory/storage 118 can include software instructions that are executed by the processor 124. In one embodiment, the communication unit 120 can employ wireless communication technology such as bluetooth, WiFi (802.11), or any other wireless technology. In one embodiment, the communication unit 120 can be a wireline communication unit that can include one or more wires for communicating electromagnetic signals and/or one or more optical fibers for communicating optical signals. The portable display unit 104 can include other components that are not illustrated, such as user interface, operating system software, display driver circuitry, A/D converters, application specific integrated circuits (ASIC), timing circuitry, and/or other power, analog, or digital circuitry. Such components will be known to those skilled in the art.

Referring now to FIG. 2, there is shown a system block diagram of another embodiment of the disclosed technology. The monitoring guidewire contains a pressure sensor and/or other sensors at the distal end. The electrical signals from the sensor(s) can be sent over a wire connection to the portable display unit. The portable display unit can include a communications port that receives external sensor input such as aortic output pressure (AO IN) from pressure transducers/hemodynamic systems (not shown). The portable display unit can also include an output communication port for outputting data to an external storage device, to another display, to a printer, and/or to a hemodynamic system (not shown).

Figure 3:
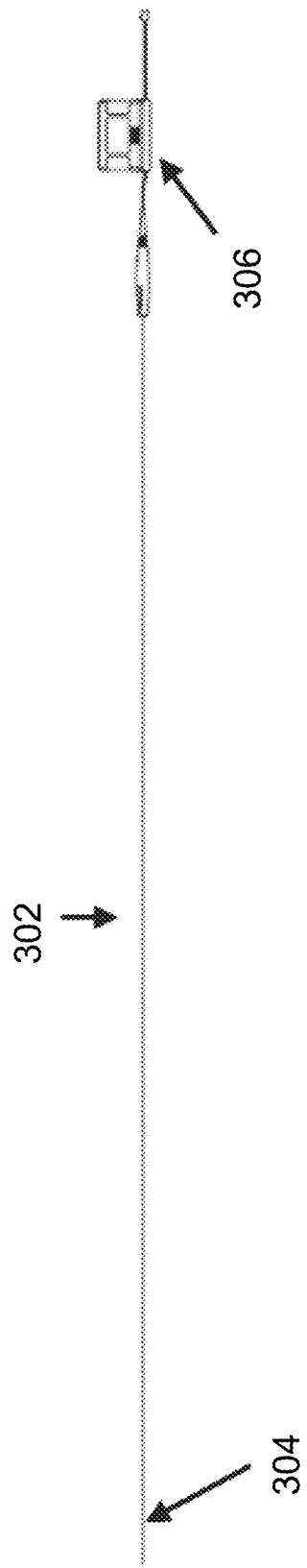
FIG. 3 is a diagram of an exemplary apparatus in accordance with the disclosed technology.

Referring now to FIG. 3, there is shown an exemplary embodiment of the disclosed intravascular diagnosis apparatus. In one embodiment, the monitoring guidewire 302 can be approximately 180 centimeters in length. In other embodiments, the monitoring guidewire 302 can be another length. The monitoring guidewire 302 can have one or more sensors in the distal region 304 of the monitoring guidewire 302. In the illustrated embodiment, the portable display unit 306 can have a small form factor such that it is a handheld display unit. In one embodiment, a handheld display unit can be equal to or less than 30 cm×30 cm×30 cm in size.

Figure 4:
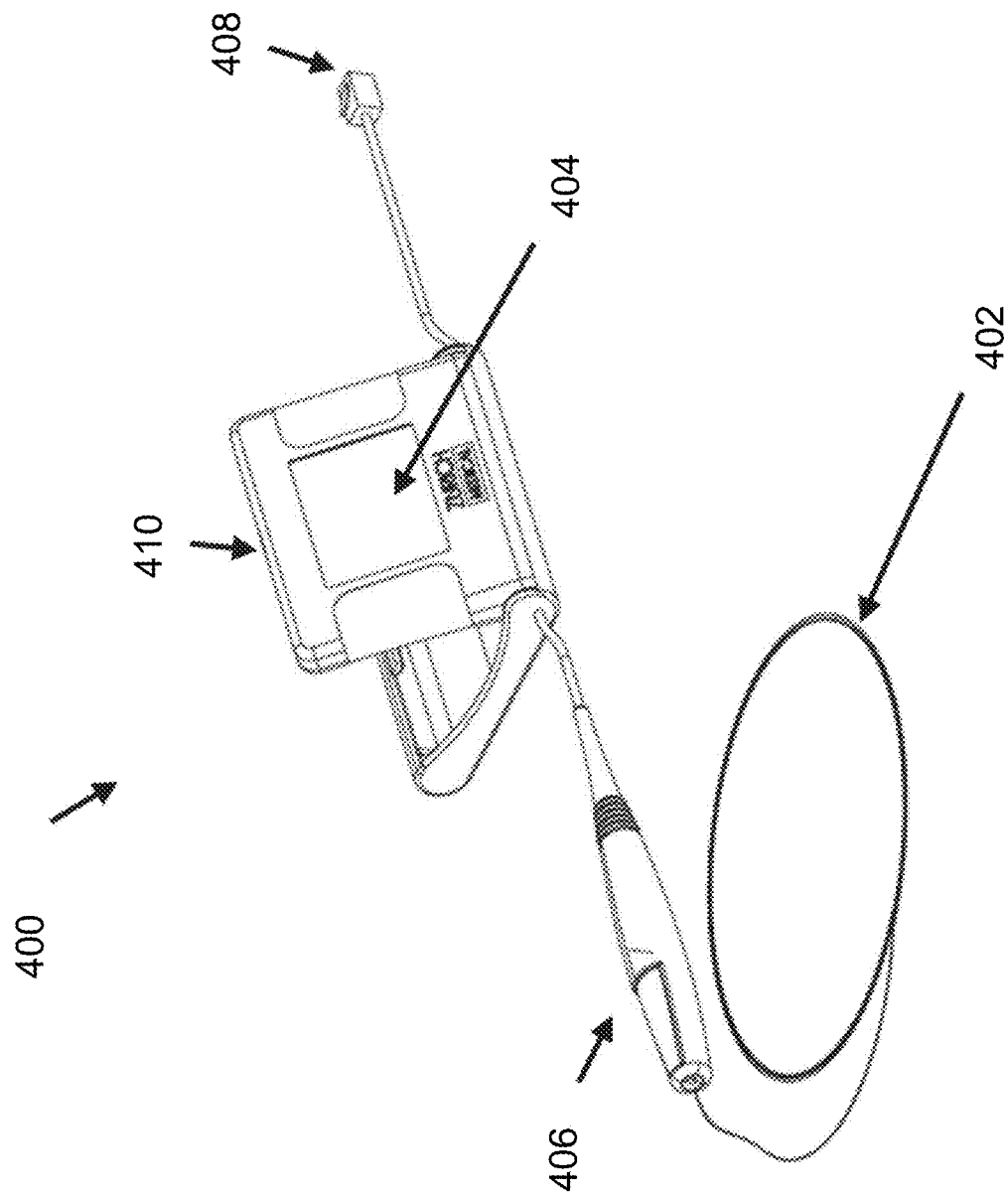
FIG. 4 is another diagram of an exemplary apparatus in accordance with the disclosed technology.

FIG. 4 is a diagram of another exemplary embodiment of the disclosed intravascular diagnosis apparatus. In the illustrated embodiment, the monitoring guidewire 402 can be attached and detached from a connector 406 of the portable display unit 400. In one embodiment, the connector 406 can include a button (not shown) which opens an aperture in the connector 406. To attach or detach the monitoring guidewire 402, a user can press and hold the button of the connector 406 and insert the monitoring guidewire 402 into the aperture until the monitoring guidewire 402 is fully inserted into connector 406. Once inserted, the user can release the button, which will then secure the monitoring guidewire 402 in place and provide a connection between the monitoring guidewire 402 and connector 406. In other embodiments, the connector 406 can engage the monitoring guidewire 402 by a screw engagement, a twist engagement, a snap engagement, or an interference fit. The described types of engagement are exemplary and do not limit the scope of the disclosed technology. Other types of ways for the connector 406 to engage the monitoring guidewire 402 are contemplated to be within the scope of the disclosed technology.

In one embodiment, the connector connection establishes a communicative connection between the monitoring guidewire 402 and the portable display unit 400. The monitoring guidewire 402 and the connector 406 can contain electrical wires that connect the monitoring guidewire 402 to the portable display unit 400 and convey signals from the monitoring guidewire sensor(s) to the portable display unit 400.

In one embodiment, the connector connection establishes a mechanical connection between the monitoring guidewire 402 and the connector 406 to control the guidewire 402 within a vasculature. In the illustrated embodiment, the connector 406 is tethered to the main housing 410 of the portable display unit 400. In one embodiment, the tether can be 6 inches to 12 inches long and can allow a user to manipulate the monitoring guidewire 402 freely without the portable display unit main housing 410 being an impediment. In one embodiment, the tether can be another length.

In one embodiment (not shown), the connector can be a connection port integrated in the portable display unit main housing 410.

In one embodiment, the connector 406 establishes a communicative connection with the monitoring guidewire 402. In one embodiment, a torquer (not shown) can be configured to engage the monitoring guidewire 402 to control the guidewire within a vasculature when the monitoring guidewire 402 is not mechanically and/or electrically connected to the connector 406. In one embodiment, the torquer can be configured to engage the monitoring guidewire 402 to control the guidewire within a vasculature when the monitoring guidewire 402 is mechanically and/or electrically connected to the connector 406. In one embodiment, the monitoring guidewire 402 does not need a torquer or the connector 406 for insertion into the vasculature of a patient and for navigation therein, and provides this capability by itself.

With continuing reference to FIG. 4, the portable display unit 400 includes a display screen 404 that can display sensor measurements and/or computed information (e.g., fractional flow reserve ratio), in numerical format and/or in waveform format. The portable display unit 400 can include one or more buttons (not shown) or a touch screen to allow a user to provide input to the portable display unit 400. In one embodiment, the screen 404 of the portable display unit can be folded in the main housing 410 before use to minimize the size of packaging when delivering the portal display unit 400. When a user takes the portable display unit 400 out of the packaging for use, the user can pivot the screen 404 from the folded position to an open position (as illustrated), providing an appropriate viewing angle to the user for the diagnosis procedure. In one embodiment, pivoting of the display screen 404 from the folded position to an open position acts as an ON switch that enables power to be delivered to the portable display unit.

In the illustrated embodiment, the portable display unit 400 also includes a communication port 408. In one embodiment, the communication port 408 allows a user to connect the portable display unit 400 to an external system (not shown). The external system can communicate a sensor signal to the portable display unit 400 through the communication port 408. In one embodiment, the sensor signal received at the communication port can be can be a pressure measurement and can be used in calculating fractional flow reserve.

Figure 5:
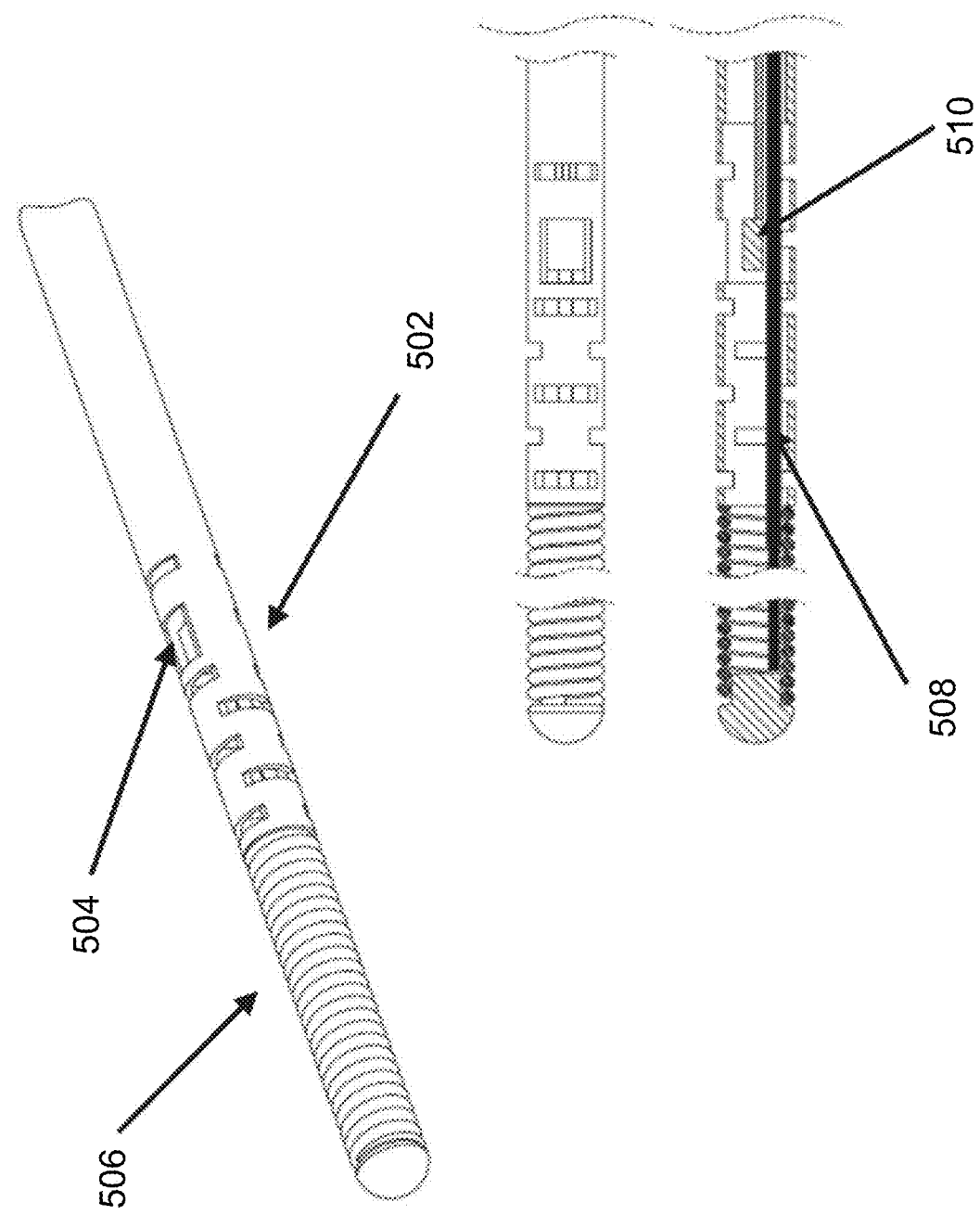
FIG. 5 is a diagram of an exemplary distal tip of the disclosed monitoring guidewire.

Referring again to FIG. 1, the monitoring guidewire 102 can include a protective structure 110 surrounding the sensor(s) 108. With reference to FIG. 5, there is shown a diagram of an exemplary protective structure 502 surrounding the sensor(s) 510 at the distal region of the monitoring guidewire. In the illustrated embodiment, the protective structure 502 is a housing that has been laser etched with a particular pattern cut to provide flexibility and/or torque translation at the distal tip or portion of the monitoring guidewire where the sensor 510 resides. The sensor(s) 510 can be situated in the laser etched housing at a window 504 in the housing so as to allow blood to contact the sensor(s) 510 in order to take sensor measurements. In the illustrated embodiment, the core wire 508 can be grinded to provide an appropriate profile for balancing flexibility and torque translation. In one embodiment, the monitoring guidewire need not include a core wire 508. Rather, the protective structure 502 can extend along the entire monitoring guidewire or a substantial portion thereof, and can be laser etched along some or all portions to provide desired flexibility and/or torque translation.

Figure 6:
FIG. 6 is a diagram of two embodiments of the distal tip of the disclosed monitoring guidewire.

Referring to FIG. 6, there is shown a diagram of two exemplary protective structures surrounding the sensor(s) at the distal region of a monitoring guidewire. One of the embodiments is a laser etched housing as described in connection with FIG. 5. The other embodiment provides a coil over the sensor(s) as the protective structure. The coil is relaxed to create a window where the sensor(s) are located to allow blood to contact the sensor(s). The illustrated embodiments are exemplary and do not limit the scope of protective structures contemplated in the disclosed technology. Other protective structures are contemplated to be within the scope of the disclosed technology.

Various aspects and embodiments of the disclosed technology have been described above. The illustrations and descriptions are merely exemplary and do not limit the scope of the disclosed technology. Even though not illustrated, various embodiments can be combined and are contemplated to fall within the scope of the disclosed technology. Furthermore, although certain features are illustrated as being in a particular location or device, the location and device are merely exemplary, and it is contemplated that various features can be located differently than as illustrated and still be within the scope of the disclosed technology.

The following description will now reference FIG. 1, and in particular, the battery 116 and the power management unit 122 of the portable display unit 104. In one aspect of the disclosed technology, the portable display unit 104 can be configured to operate for a predetermined duration or for a predetermined number of uses, and then be disposed. The battery 116 and/or power management unit 122 can implement these features so that the portable display unit 104 can be inoperable after being used for a particular duration or for a particular number of diagnosis procedures. Even so, the portable display unit 104 can be disposed while it is still operable, prior to it being inoperable.

In one embodiment, the predetermined duration can correspond to the approximate length of time of a single intravascular diagnosis procedure. In one embodiment, the predetermined duration can correspond to the approximate length of time of multiple diagnosis procedures, such as three procedures. In one embodiment, the predetermined duration can be twelve hours or twenty-four hours or several days. In one aspect of the disclosed technology, the portable display unit 104 can include one or more batteries 116 that are configured to power the portable display unit 104 for the desired duration, such that the batteries 116 are substantially depleted at the end of the desired duration. In one embodiment, the one or more batteries 116 are non-rechargeable, so that the portable display unit 104 is disposed after the batteries 116 are depleted. In one embodiment, the power management unit 122 can control the operating time of the portable display unit 104 by preventing the portably display unit 104 from powering down after the display screen 114 is turned on. In such an embodiment, the portable display unit 104 will operate continuously until the batteries 116 are depleted or substantially depleted. The portable display unit 104 can be disposed prior to the batteries 116 being depleted, while the portable display unit 104 is still operable.

In one embodiment, the portable display unit 104 can track the number of diagnosis procedures performed and can be configured to be inoperable after a particular number of procedures has been performed. In one embodiment, the portable display unit 104 can track the number of diagnosis procedures performed by the number of times the portable display unit 114 has been turned on and/or off. In one embodiment, the portable display unit 104 can be configured to be inoperable after a single diagnosis procedure has been performed. In one aspect of the disclosed technology, the power management unit 122 can prevent the portable display unit 104 from being powered on after the particular number of procedures has been reached. The batteries 116 can be rechargeable and can be recharged by a power source of the portable display unit 104 and/or by a power source external to the portable display unit 104. Even when the batteries 116 are not yet depleted, the power management unit 122 can cause the portable display unit 104 to be inoperable by preventing the batteries 116 from powering the portable display unit 104.

The intravascular diagnosis procedure will now be described with continuing reference to FIG. 1 and with reference to FIGS. 7-11. Diagnosing the severity of one or more stenoses within the vasculature of a patient has been studied based on hemodynamic pressure measurements distal to a stenosis in comparison with aortic output pressure. The ratio of pressure distal to a stenosis to the aortic output pressure is known as "factional flow reserve", or FFR. The value of the FFR indicates the severity of the stenosis, and clinical data provides guidance on the type of surgical procedure that would be effective for particular FFR ranges.

The disclosed technology includes multiple ways of computing FFR, including what will be referred to herein as "push-forward FFR", "pull-back FFR", and "simultaneous FFR". Each of these can be implemented by software code or machine code stored in memory/storage 118 of the portable display unit 104 (FIG. 1). The processor 124 can execute the software code to compute the FFR, and the resulting information can be displayed on the display screen 114. Each of the computation methods will now be described.

Simultaneous Fraction Flow Reserve

Figure 9:
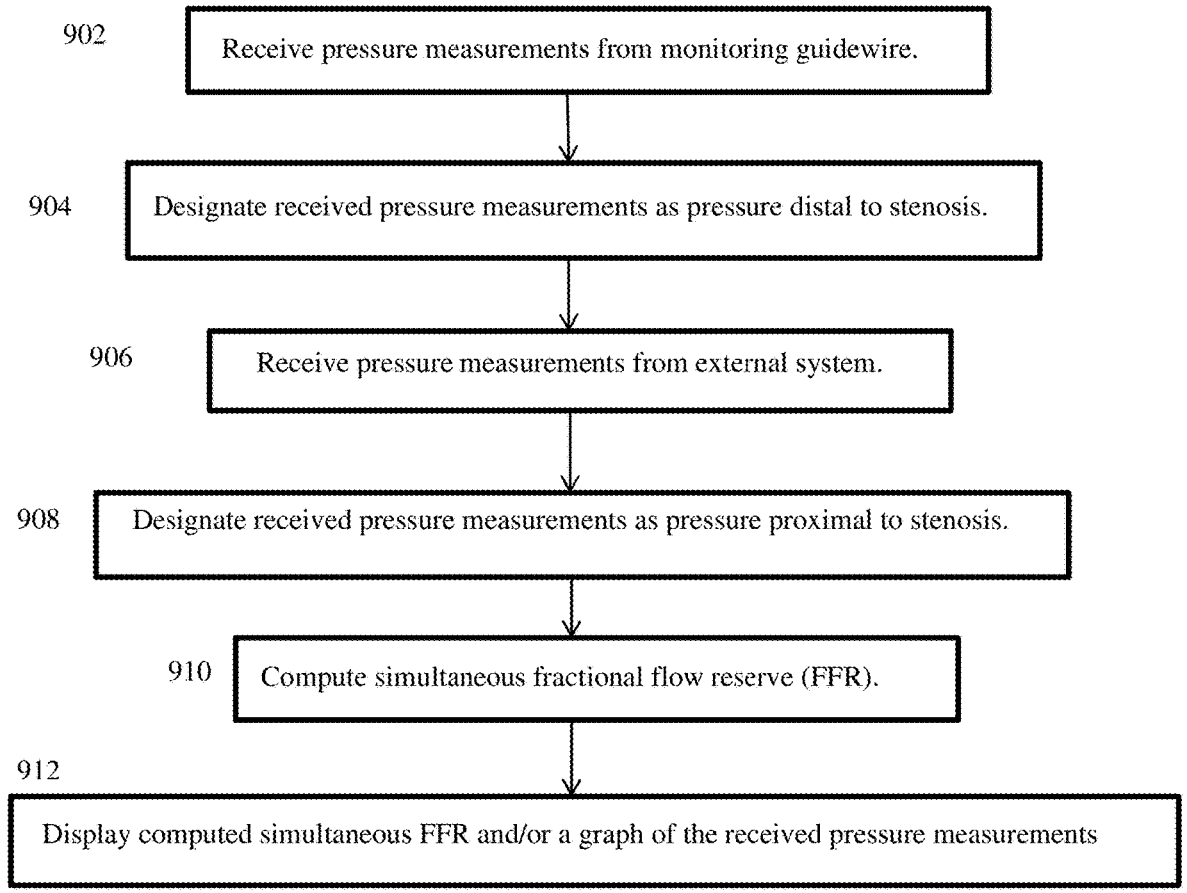
FIG. 9 is a flow diagram of exemplary operation of the disclosed technology for computing simultaneous fractional flow reserve.
Figure 10:
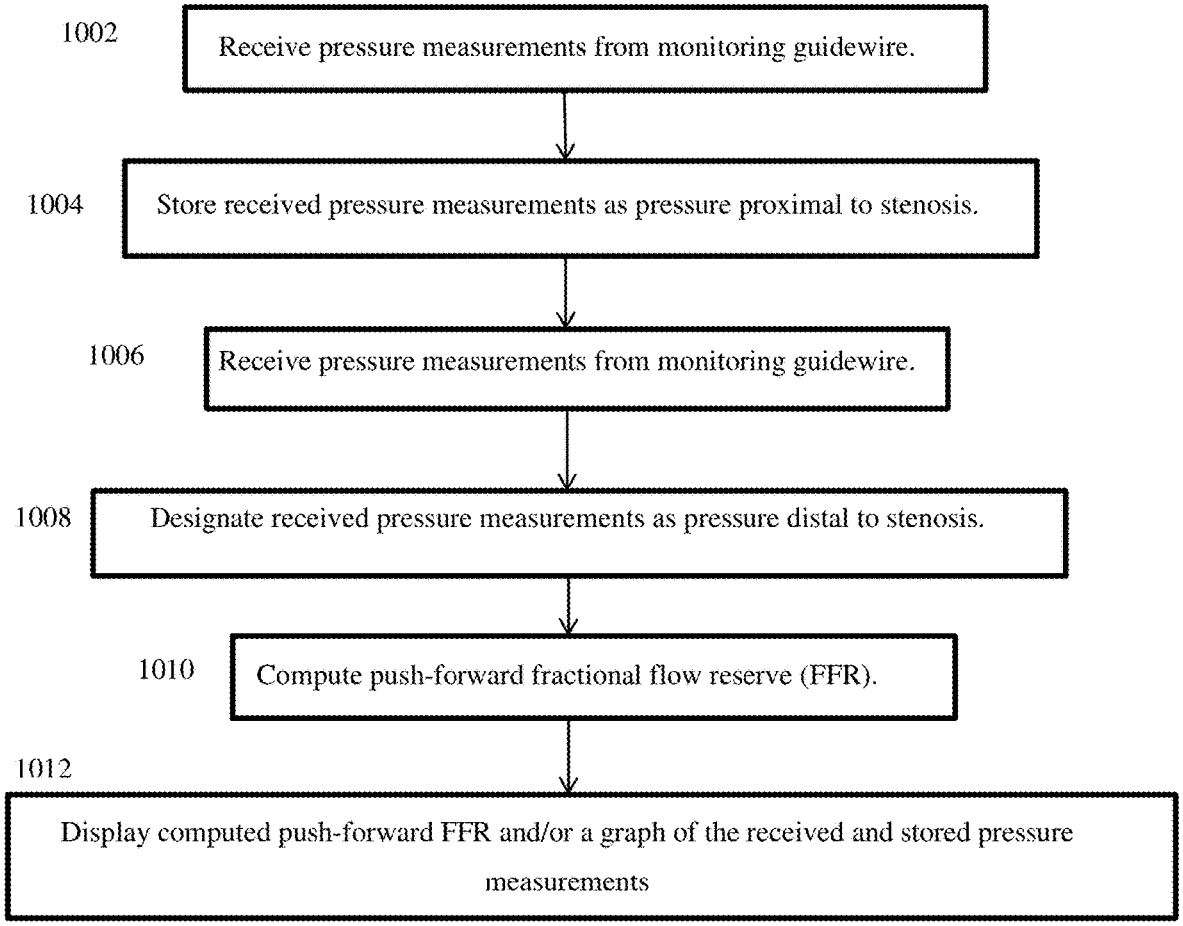
FIG. 10 is a flow diagram of exemplary operation of the disclosed technology for computing push-forward fractional flow reserve.
Figure 11:
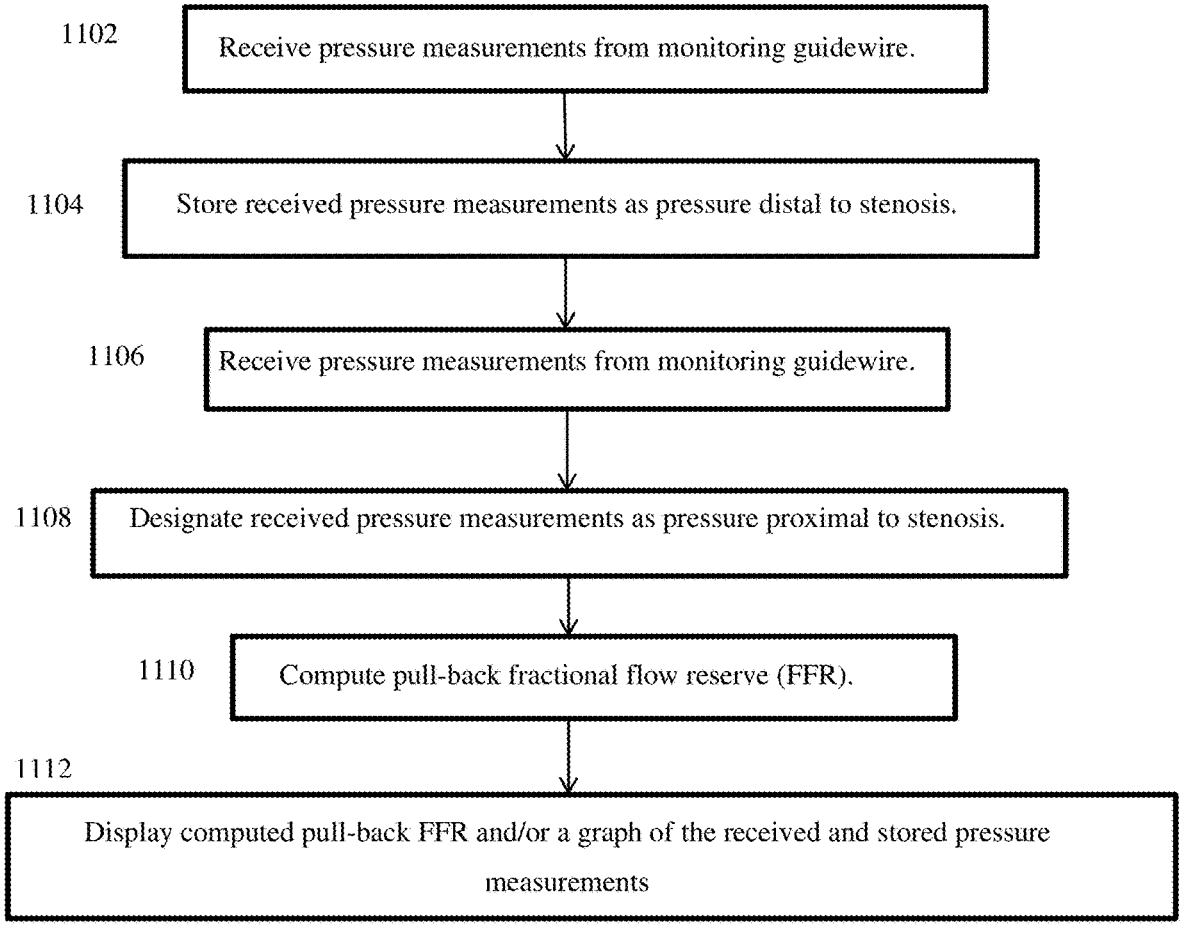
FIG. 11 is a flow diagram of exemplary operation of the disclosed technology for computing pull-back fractional flow reserve.

Simultaneous FFR involves simultaneous pressure readings from two separate pressure sensors, and a computation of FFR in real-time as the pressure readings from the two separate pressure sensors are received. Referring to FIG. 1 and FIG. 9, one pressure sensor is located in the monitoring guidewire 102, and is used to measure pressure distal to a stenosis in a patient. The pressure readings can be communicated by the communication unit 112 of the monitoring guidewire 102 to the communication unit 120 of the portable display unit 104 (902). This communication can be a wireless communication or can be a wireline communication through, for example, the connector illustrated in FIG. 3. The other pressure sensor can measure aortic output pressure and is external to the apparatus 100 of FIG. 1. The portable display unit 104 can designate the received pressure measurements as pressure distal to a stenosis (904). The external sensor readings can be communicated to the communication unit 120 of the portable display unit by, for example, the communication port illustrated in FIG. 3 (906). The portable display unit 104 can designate the received pressure measurements as pressure proximal to a stenosis (908). The portable display unit 104 can compute the simultaneous FFR as the pressure measurements are received (910), by the formula: $FFR=(P_{sensor}-P_{ra})/(P_{port}-P_{ra})$, where:

$P_{port}$ are moving means over time of real-time pressure measurements received at the communications port, $P_{sensor}$ are moving means over time of real-time pressure measurements from the pressure sensor in the distal region of the core wire of the monitoring guidewire, and $P_{ra}$ is a constant, which can be zero or another constant value.

In one embodiment, the moving means over time can compute the mean over a window of time that spans one heartbeat. In other embodiments, the window of time can span less than one heartbeat or more than one heartbeat. As new sensor measurements are received over time (902, 906), the window can include newer measurements and remove older measurements to compute the moving means.

The portable display unit 104 can receive pressure measurements and can compute the simultaneous FFR based on the received measurements. The portable display unit 104 can store the received pressure measurements and/or the computed simultaneous FFR in memory/storage 118, and can display the computed simultaneous FFR and/or a graph of the received pressure measurements on the display screen 114 (912).

Push-Forward Fractional Flow Reserve

Figure 8:
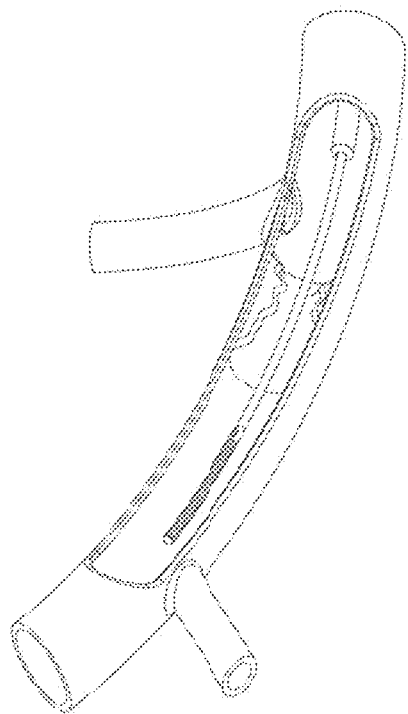
FIG. 8 is a diagram of another position for the disclosed monitoring guidewire for estimating fractional flow reserve.
Figure 7:
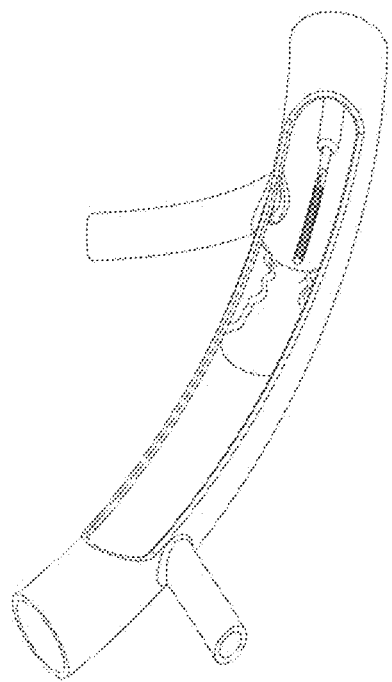
FIG. 7 is a diagram of one position for the disclosed monitoring guidewire for estimating fractional flow reserve.

In contrast to simultaneous FFR, the push-forward FFR does not receive external pressure measurements. With continuing reference to FIG. 1, push-forward FFR is computed using pressure measurements from only the pressure sensor(s) 108 in the distal region of the monitoring guidewire 102. Using traditional angiography, a stenosis can be located and, as shown in FIG. 8, the monitoring guidewire can be inserted into a patient to a point proximal to the stenosis. Pressure can be measured at this position by the sensor(s) 108 and communicated by the communication unit 112 to the portable display unit 104 (1002). The portable display unit 104 can store the measurements in this position in the memory/storage 118 as pressure proximal to a stenosis (1004). Next, the monitoring guidewire 102 can be pushed forward past the stenosis to a point distal to the stenosis, as illustrated in FIG. 7. Pressure can be measured at this position by the sensor(s) 108 and communicated by the communication unit 112 to the portable display unit 104 (1006). The portal display unit 104 can designate the pressure measurements received at this position as pressure distal to the stenosis (1008). The processor 124 can compute the push-forward FFR (1010) by the formula: $FFR=(P_{sensor}-P_{ra})/(P_{saved}-P_{ra})$, where:

$P_{saved}$ are moving means over time of recorded pressure measurements proximal to the stenosis, $P_{sensor}$ are moving means over time of real time pressure measurements distal to the stenosis, and $P_{ra}$ is a constant, which can be zero or another constant value.

Aspects of computing the moving means over time were described above in connection with simultaneous FFR, and such aspects apply to push-forward FFR as well.

The portal display unit 104 can display the computed push-forward FFR and/or a graph of the received and stored pressure measurements (1012).

Push-forward FFR can be computed in the case of one stenosis and can also be computed in the case of multiple stenosis. In either case, $P_{saved}$ are moving means over time of pressure measurements proximal to all of the stenosis. In one embodiment, $P_{saved}$ are moving means over time computed based on recorded pressure measurements. In one embodiment, $P_{saved}$ are moving means over time computed and recorded as pressure measurements are received, and the pressure measurements may or may not be recorded. For example, in the case of two stenoses, $P_{saved}$ are based on pressure measurements proximal to both the first and second stenosis. When the monitoring guidewire pressure sensor 108 is pushed forward to a position between the first and the second stenosis, $P_{sensor}$ are based on real time pressure measurements between the two stenoses. Push-forward FFR can be calculated in this position and displayed on the display screen 114. When the monitoring guidewire pressure sensor 108 is pushed forward to a position distal to both the first and second stenoses, $P_{sensor}$ are based on real time pressure measurements distal to both of the two stenoses. Push-forward FFR can be calculated in this position and displayed on the display screen 114. Thus, push-forward FFR enables FFR to be computed and displayed as the monitoring guidewire 102 is pushed forward across one or more stenoses in a blood vessel lumen. The only measurements and/or moving means that need to be recorded for push-forward FFR computations are pressure measurements and/or moving means of pressure measurements proximal to all stenoses, and this is performed at the outset.

Pull-Back Fractional Flow Reserve

Similar to push-forward FFR, the pull-back FFR does not receive external pressure measurements. Rather, pull-back FFR is computed using pressure measurements from only the pressure sensor(s) 108 in the distal region of the monitoring guidewire 102. Using traditional angiography, a stenosis can be located and, as shown in FIG. 7, the monitoring guidewire can be inserted into a patient to a point distal to the stenosis. Pressure can be measured at this position by the sensor(s) 108 and communicated by the communication unit 112 to the portable display unit 104 (1102). The portable display unit 104 can store the measurements in this position in the memory/storage 118 as pressure distal to a stenosis (1104). Next, the monitoring guidewire 102 can be pulled back through the stenosis to a point proximal to the stenosis, as illustrated in FIG. 8. Pressure can be measured at this position by the sensor(s) 108 and communicated by the communication unit 112 to the portable display unit 104 (1106). The portable display unit 104 can designate the measurements received in this position as pressure proximal to a stenosis (1108). The processor 124 can compute the pull-back FFR (1110) by the formula:

$$FFR=(P_{saved}-P_{ra})/(P_{sensor}-P_{ra})$$

where:

$P_{saved}$ are moving means over time of recorded pressure measurements distal to the stenosis, $P_{sensor}$ are moving means over time of real time pressure measurements proximal to the stenosis, and $P_{ra}$ is a constant, which can be zero or another constant value.

Aspects of computing the moving means over time were described above in connection with simultaneous FFR, and such aspects apply to pull-back FFR as well.

The portal display unit 104 can display the computed pull-back FFR and/or a graph of the received and stored pressure measurements (1112).

Pull-back FFR can be computed in the case of one stenosis and can also be computed in the case of multiple stenosis. In either case, $P_{sensor}$ are based on real-time pressure measurements proximal to all of the stenosis, which are the final pressure measurements that are taken. For example, in the case of two stenoses, the monitoring guidewire pressure sensor 108 is initially placed at a position distal to both the first and the second stenoses. Pressure can be measured at this position by the sensor(s) 108 and communicated by the communication unit 112 to the portable display unit 104. In one embodiment, $P_{saved\_d1}$ are moving means over time computed later based on recorded pressure measurements. In one embodiment, $P_{saved\_d1}$ are moving means over time computed and recorded while the pressure measurements are received in this position, and the pressure measurements may or may not be recorded. The memory/storage 118 can record the pressure measurements in this position and/or computed moving means over time based on such pressure measurements. Pull-back FFR cannot yet be calculated because there is no real-time measurement yet proximal to all of the stenoses. Next, the monitoring guidewire 102 can be pulled back through the first stenosis to a point between the first and second stenosis. Pressure can be measured at this position by the sensor(s) 108 and communicated by the communication unit 112 to the portable display unit 104. In one embodiment, $P_{saved\_d2}$ are moving means over time computed later based on recorded pressure measurements. In one embodiment, $P_{saved\_d1}$ are moving means over time computed and recorded while the pressure measurements are received in this position, and the pressure measurements may or may not be recorded. The memory/storage 118 can record the pressure measurements in this position and/or computed moving means over time based on such pressure measurements. Once again, pull-back FFR cannot yet be calculated because there is no real-time measurement yet proximal to all of the stenoses. Lastly, the monitoring guidewire 102 can be pulled back through the second stenosis to a point proximal to both the first and second stenosis. Real-time pressure can be measured at this position by the sensor(s) 108 and communicated by the communication unit 112 to the portable display unit 104. Only at this point are there enough measurements to compute the two pull-back FFR: $FFR_1=(P_{saved\_d1}-P_{ra})/(P_{sensor}-P_{ra})$ and $FFR_2=(P_{saved\_d2}-P_{ra})/(P_{sensor}-P_{ra})$. Therefore, pull-back FFR does not allow FFR to be calculated and displayed as the monitoring guidewire is being pulled back through multiple stenoses.

Accordingly, three computations for fractional flow reserve have been described above in connection with FIGS. 7-11. In one aspect of the disclosed technology, and with reference to FIG. 1, the portable display unit 104 is configured with capability to compute fractional flow reserve using any of the three ways. In one embodiment, the portable display unit 104 can be configured to automatically use one of the three ways of computing fractional flow reserve. In one embodiment, the portable display unit 104 can be configured to automatically select one of the three ways of computing fractional flow reserve when a condition is present and to automatically select another of the three ways of computing fractional flow reserve when other conditions are present. In one embodiment, the portable display unit 104 can be configured to permit a user to manually select one of the three ways of computing fraction flow reserve.

The disclosed technology measures pressure and calculates fractional flow reserve (FFR). FFR is a calculation that has been clinically demonstrated to assist in determining whether to treat or not to treat an intermediate coronary lesion. Using the disclosed technology will thus assist a physician in determining what to do with an intermediate lesion. The disclosed FFR equations are exemplary and do not limit the scope of the disclosed technology. Other ways to compute FFR are contemplated to be within the scope of the disclosed technology.

Referring again to FIG. 3 and FIG. 4, monitoring guidewires 302/402 in accordance with the disclosed technology have been described above herein. Various embodiments of the monitoring guidewire will now be described with respect to FIGS. 12-15.

Figure 12:
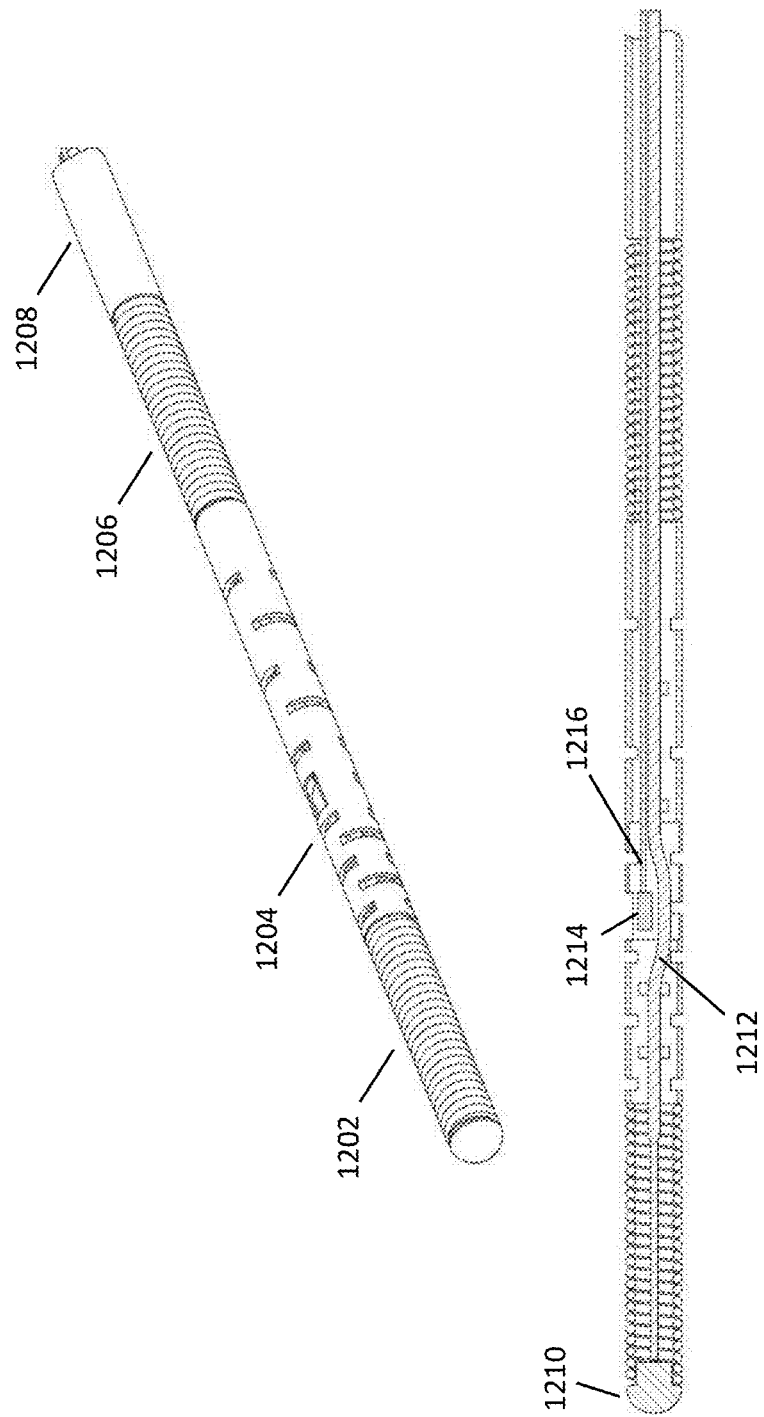
FIG. 12 is a diagram of a perspective view and a cross-sectional view of one embodiment of the disclosed monitoring guidewire.

FIG. 12 shows a perspective view and a cross-sectional view of one embodiment of a monitoring guidewire. The illustrated guidewire housing includes four segments: a distal coil 1202, a slotted tube 1204, an intermediate coil 1206, and a non-slotted proximal tube 1208. The slotted tube 1204 can include a slot pattern that is configured to provide desired properties and characteristics, such as flexibility and/or torque control. The illustrated pattern is merely exemplary and other patterns are contemplated to be within the scope of the disclosed technology. The distal coil 1202 and the intermediate coil 1206 can be configured to provide desired characteristics, such as torsion and/or compression. Referring to the cross-sectional view shown in FIG. 12, the illustrated monitoring guidewire includes an atraumatic tip 1210, a core wire 1212, one or more sensors 1214, and one or more signal wires 1216.

Figure 15:
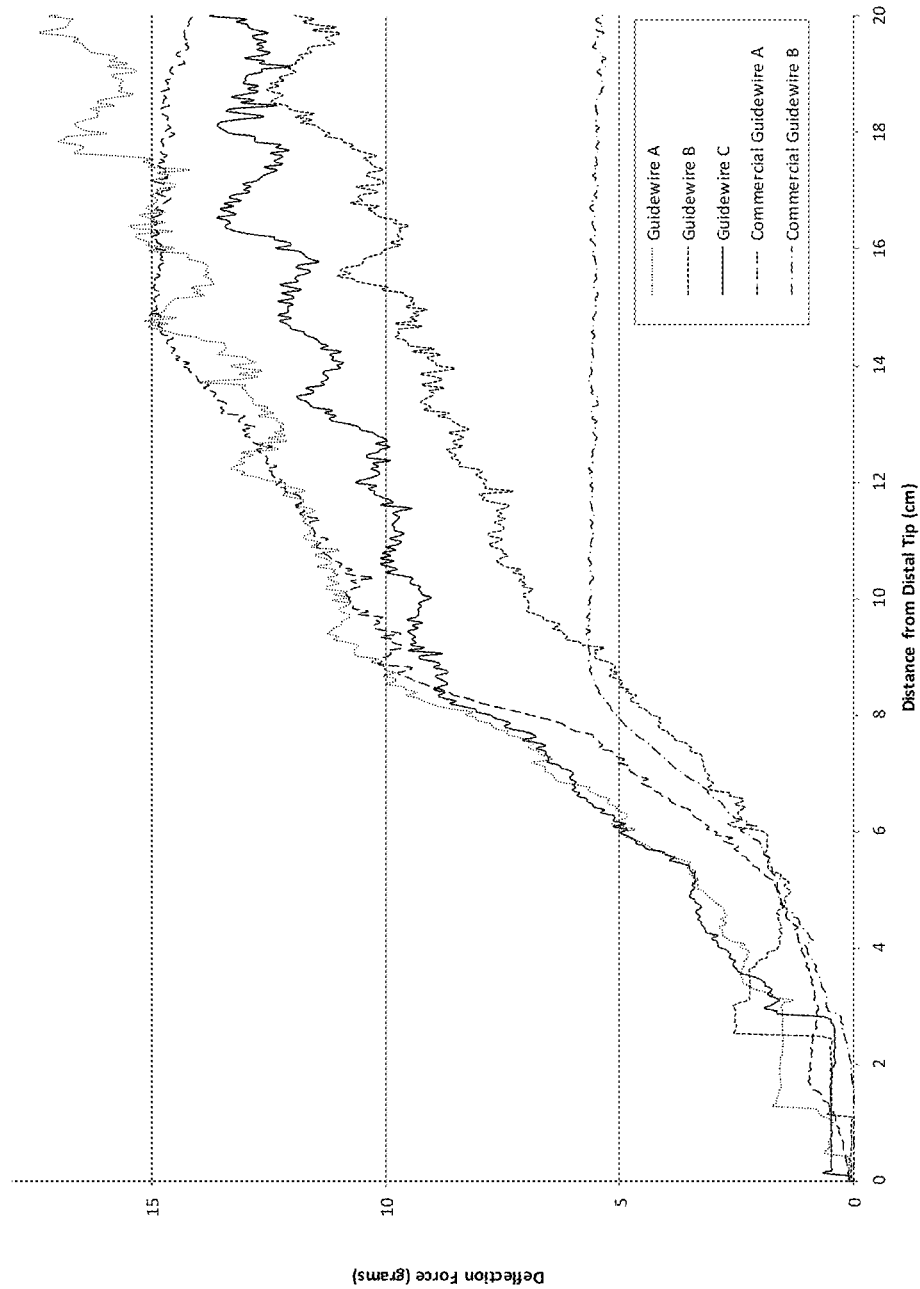
FIG. 15 is a diagram of exemplary characteristics of the disclosed monitoring guidewire.

In one aspect of the disclosed technology, the illustrated monitoring guidewire can provide a torque response that approximates that of a 0.014 inch workhorse guidewire. One skilled in the art will understand the properties of a workhorse guidewire, including, but not limited to, torque control, trackability, steerability, flexibility, prolapse tendency, radiopacity/visibility, tactile feedback, crossing, and support. Various of these properties are described in Erglis et al, "*Tools & Techniques: coronary guidewires*", EuroIntervention 2010, 6:1-8, and in Goldberg et al, "*Guidewires—Expert Round Table*", US Cardiology—Volume 5 Issue 1; 2008:5(1):34-38. The entire contents of these articles are hereby incorporated by reference herein. A workhorse guidewire provides balancing of various properties to allow the guidewire to track through vessels, access lesions, cross lesions atraumatically, and provide support for interventional devices that use the guidewire as a track during deployment. For example, torque control and flexibility allow a guidewire to rotate and bend to navigate through vessels, but balance between these two properties is needed—more torque control results in less flexibility, and more flexibility results in less torque control. Certain properties of workhorse guidewires can be quantified, such as flexibility, prolapse, and support. Examples of quantifying such properties in terms of deflection force along the length of a guidewire are shown in FIG. 15. The graph of FIG. 15 was generated by deflecting points along a guidewire at a particular angle and measuring the force with which the guidewire resisted the deflection. Generally, a greater deflection force at a particular point indicates that the guidewire is less flexible at that point but provide more support at that point.

Referring again to FIG. 12, in one embodiment, the four segments 1202-1208 can have an outer diameter between 0.013 and 0.014 inches, and an inner diameter less than 0.011 inches. The core wire 1212 can have a diameter of at most 0.007 inches. The four segments 1202-1208 altogether can be referred to as a "housing". The housing can total to approximately 177-180 centimeters in length, which can be substantially coextensive with the core wire 1212 or slightly shorter than the core wire 1212.

One or more of the four housing segments 1202-1208 can be made of a material that is more flexible, deflectable or bendable than the material of the core wire 1212, or less stiff or less rigid than the material of the core wire 1212, or provides more flexibility, deflectability or bendability than the material of the core wire 1212. The core wire 1212 can be made of MP35N, L605, Elgiloy, and/or an alloy of nickel, cobalt, molybdenum and chromium. Generally, 0.014 inch workhorse guidewires could not use MP35N, L605, Elgiloy, or an alloy of nickel, cobalt, molybdenum and chromium, because the material stiffness at 0.014 inches lacks the flexibility and atraumatic characteristics required by a workhouse guidewire to maneuver in the coronary arteries. The disclosed technology provides a guidewire with the characteristics of a 0.014 inch workhorse guidewire while using such materials. The MP35N, L605, Elgiloy, or alloy of nickel, cobalt, molybdenum and chromium are used for the core wire 1212, which can be smaller in diameter than the usual 0.014 inch workhorse guidewire. For example, the core wire 1212 that can be at most 0.007 inches in diameter. Such a combination of material and diameter size can provide the torque translation and steerability of a 0.014 in workhorse guidewire. To provide the flexibility and atraumatic characteristics of a 0.014 workhorse guidewire, the disclosed technology provides a housing 1202-1208 that is more flexible, deflectable or bendable, or less stiff or less rigid, than the core wire 1212. One or more of the four housing segments 1202-1208 can be made of polyemide, nitinol, various types or composition of stainless steel (e.g., 304 & 304 High Tensile), nylon, polyurethane, silicone, or PTFE. In one embodiment, the entire housing 1202-1208 can be more flexible, deflectable or bendable, or less stiff or less rigid, than the core wire 1212. In one embodiment, a distal portion of the housing 1202-1208 can be more flexible, deflectable or bendable, or less stiff or less rigid, than the core wire 1212, such as a 40 cm segment of a distal portion of the housing.

Figure 13:
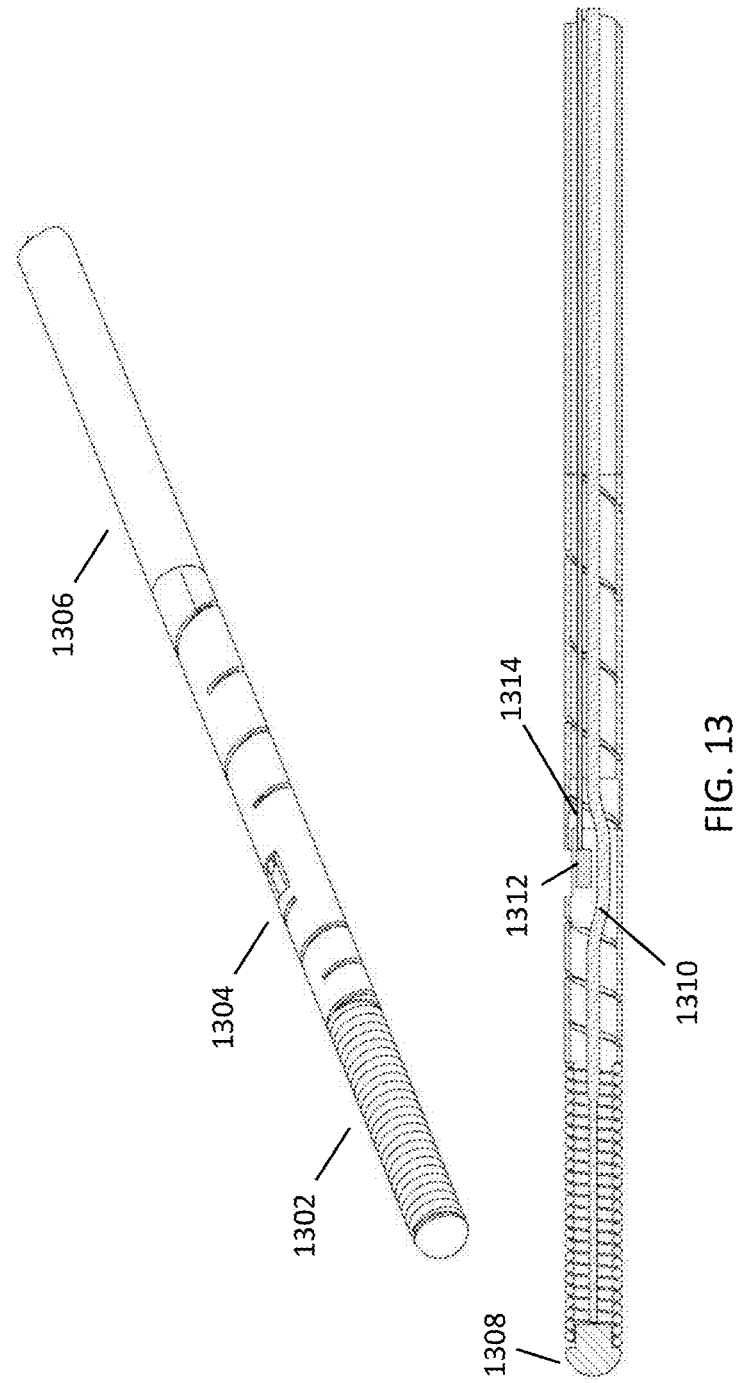
FIG. 13 is a diagram of a perspective view and a cross-sectional view of another embodiment of the disclosed monitoring guidewire.

FIG. 13 shows a perspective view and a cross-sectional view of another embodiment of the disclosed monitoring guidewire. The illustrated guidewire housing includes three segments: a distal coil 1302, a slotted tube 1304, and a non-slotted proximal tube 1306. The illustrated embodiment includes one fewer segment than the embodiment of FIG. 12, which can potentially decrease manufacturing difficulties and increase manufacturing yield. The slotted tube 1304 can include a slot pattern that is configured to provide desired properties and characteristics, such as flexibility and/or torque control. The illustrated pattern is merely exemplary and other patterns are contemplated to be within the scope of the disclosed technology. The distal coil 1302 can be configured to provide desired characteristics, such as torsion and/or compression. Referring to the cross-sectional view shown in FIG. 13, the illustrated monitoring guidewire includes an atraumatic tip 1308, a core wire 1310, one or more sensors 1312, and one or more signal wires 1314.

The illustrated monitoring guidewire can provide torque control that approximates that of a 0.014 inch workhorse guidewire. In one embodiment, the three segments 1302-1306 can have an outer diameter between 0.013 and 0.014 inches, and an inner diameter less than 0.011 inches. The core wire 1310 can have a diameter of at most 0.007 inches. The three segments 1302-1306 altogether can be referred to as a "housing". The housing can total to approximately 177-180 centimeters in length, which can be substantially coextensive with the core wire 1310 or slightly shorter than the core wire 1310.

One or more of the three housing segments 1302-1306 can be made of a material that is more flexible, deflectable or bendable than the material of the core wire 1310, or less stiff or less rigid than the material of the core wire 1310, or provides more flexibility, deflectability or bendability than the material of the core wire 1310. The core wire 1310 can be made of MP35N, L605, Elgiloy, and/or an alloy of nickel, cobalt, molybdenum and chromium. The core wire 1310 can be smaller in diameter than the usual 0.014 inch workhorse guidewire. For example, the core wire 1310 can be at most 0.007 inches in diameter. Such a combination of material and diameter size can provide the torque translation and steerability of a 0.014 in workhorse guidewire. To provide the flexibility and atraumatic characteristics of a 0.014 workhorse guidewire, the disclosed technology provides a housing 1302-1306 that is more flexible, deflectable or bendable, or less stiff or less rigid, than the core wire 1310. One or more of the three housing segments 1302-1306 can be made of polyemide, nitinol, various types or composition of stainless steel (e.g., 304 & 304 High Tensile), nylon, polyurethane, silicone, or PTFE. In one embodiment, the entire housing 1302-1306 can be more flexible, deflectable or bendable, or less stiff or less rigid, than the core wire 1310. In one embodiment, a distal portion of the housing 1302-1306 can be more flexible, deflectable or bendable, or less stiff or less rigid, than the core wire 1310, such as a 40 cm segment of a distal portion of the housing.

Figure 14:
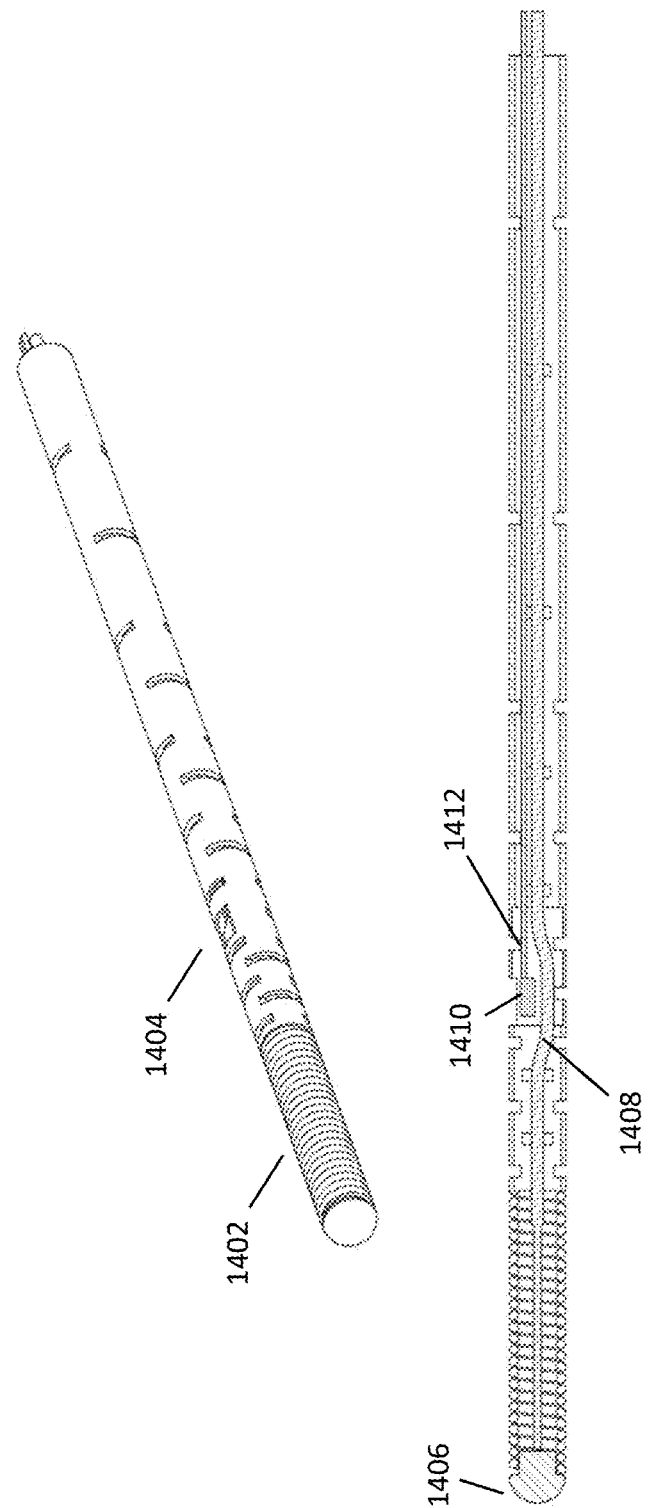
FIG. 14 is a diagram of a perspective view and a cross-sectional view of yet another embodiment of the disclosed monitoring guidewire.

FIG. 14 shows a perspective view and a cross-sectional view of another embodiment of the disclosed monitoring guidewire. The illustrated guidewire housing includes two segments: a distal coil 1402 and a tube 1404 having a slotted distal portion and the remainder being non-slotted. The illustrated embodiment includes one fewer segment than the embodiment of FIG. 13, which can potentially decrease manufacturing difficulties and increase manufacturing yield. The tube 1404 can include a slot pattern that is configured to provide desired properties and characteristics, such as flexibility and/or torque control. The illustrated pattern is merely exemplary and other patterns are contemplated to be within the scope of the disclosed technology. The distal coil 1402 can be configured to provide desired characteristics, such as torsion and/or compression. Referring to the cross-sectional view shown in FIG. 14, the illustrated monitoring guidewire includes an atraumatic tip 1406, a core wire 1408, one or more sensors 1410, and one or more signal wires 1412.

The illustrated monitoring guidewire can provide torque control that approximates that of a 0.014 inch workhorse guidewire. In one embodiment, the two segments 1402-1404 can have an outer diameter between 0.013 and 0.014 inches, and an inner diameter less than 0.011 inches. The core wire 1408 can have a diameter of at most 0.007 inches. The two segments 1402-1404 altogether can be referred to as a "housing". The housing can total to approximately 177-180 centimeters in length, which can be substantially coextensive with the core wire 1408 or slightly shorter than the core wire 1408.

One or both of the two housing segments 1402-1404 can be made of a material that is more flexible, deflectable or bendable than the material of the core wire 1408, or less stiff or less rigid than the material of the core wire 1408, or provides more flexibility, deflectability or bendability than the material of the core wire 1408. The core wire 1408 can be made of MP35N, L605, Elgiloy, and/or an alloy of nickel, cobalt, molybdenum and chromium. The core wire 1408 can be smaller in diameter than the usual 0.014 inch workhorse guidewire. For example, the core wire 1408 that can be at most 0.007 inches in diameter. Such a combination of material and diameter size can provide the torque translation and steerability of a 0.014 in workhorse guidewire. To provide the flexibility and atraumatic characteristics of a 0.014 workhorse guidewire, the disclosed technology provides a housing 1402-1404 that is more flexible, deflectable or bendable, or less stiff or less rigid, than the core wire 1408. One or both of the two housing segments 1402-1404 can be made of polyemide, nitinol, various types or composition of stainless steel (e.g., 304 & 304 High Tensile), nylon, polyurethane, silicone, or PTFE. In one embodiment, the entire housing 1402-1404 can be more flexible, deflectable or bendable, or less stiff or less rigid, than the core wire 1408. In one embodiment, a distal portion of the housing 1402-1404 can be more flexible, deflectable or bendable, or less stiff or less rigid, than the core wire 1408, such as a 40 cm segment of a distal portion of the housing.

Various embodiments for a monitoring guidewire have been described above with reference to the drawings. The slots of the slotted tube segments may have different shapes and patterns than those illustrated. The segments may have different dimensions than those illustrated or described.

Various aspects and embodiments of the disclosed technology have been described above. The illustrations and descriptions are merely exemplary and do not limit the scope of the disclosed technology. Even though not illustrated, various embodiments can be combined and are contemplated to fall within the scope of the disclosed technology. Furthermore, although certain features are illustrated as being in a particular location or device, the location and device are merely exemplary, and it is contemplated that various features can be located differently than as illustrated and still be within the scope of the disclosed technology.

The illustrations, embodiments, and specifications disclosed herein are exemplary and do not limit the spirit and scope of the disclosed technology. Combinations of one or more disclosed embodiments or specification, or portions of one or more embodiments or specifications, are contemplated as being within the scope of the disclosed technology.

What is claimed is:

1. A monitoring guidewire comprising:
    a core wire comprising a distal region made of at least one of: MP35N, L605, Elgiloy, or an alloy of nickel, cobalt, molybdenum and chromium;
    a sensor disposed in the distal region of the core wire;
    a housing substantially coextensive with the core wire and surrounding the core wire, the housing being more flexible than the core wire for at least the distal region of the housing; and
    at least one signal wire connected to the sensor and positioned within the housing,
    wherein the core wire has a widest diameter of at most 0.007 inches,
    wherein the housing comprises a laser etched hypotube having an outer diameter between 0.013 and 0.014 inches and having an inner diameter less than 0.011 inches, and
    wherein the core wire and the housing together have quantifiable flexibility, prolapse, support, and deflection force characteristics that approximate those of a 0.014 inch workhorse guidewire.

2. The monitoring guidewire of claim 1, wherein the housing is more flexible than the core wire for at most a 40 cm length of the distal portion of the housing.

3. The monitoring guidewire of claim 1, wherein the housing is more flexible than the core wire for an entire length of the housing.

4. The monitoring guidewire of claim 1, wherein the housing further comprises a protective structure surrounding the sensor, and a distal coil.

5. A monitoring guidewire comprising:
    a core wire having a first entire length and comprising a distal region made of at least one of: MP35N, L605, Elgiloy, or an alloy of nickel, cobalt, molybdenum and chromium;
    a sensor disposed in the distal region of the core wire;
    a housing surrounding the core wire and having a second entire length that is slightly less than the first entire length; and
    at least one signal wire connected to the sensor and positioned within the housing,
    wherein the core wire has a widest diameter of at most 0.007 inches,
    wherein the housing comprises a laser etched hypotube having an outer diameter between 0.013 and 0.014 inches and having an inner diameter less than 0.011 inches, and
    wherein the core wire and the housing together have quantifiable flexibility, prolapse, support, and deflection force characteristics that approximate those of a 0.014 inch workhorse guidewire.

6. The monitoring guidewire of claim 5, wherein the housing is more flexible than the core wire for at most a 40 cm length of a distal portion of the housing.

7. The monitoring guidewire of claim 5, wherein the housing is more flexible than the core wire for an entire length of the housing.

8. The monitoring guidewire of claim 5, wherein the housing further comprises a protective structure surrounding the sensor and a distal coil.

* * * * *